US009005587B2

(12) United States Patent
LeGeros et al.

(10) Patent No.: US 9,005,587 B2
(45) Date of Patent: Apr. 14, 2015

(54) ANTI-BACTERIAL AND MINERALIZING CALCIUM PHOSPHATE COMPOSITIONS

(75) Inventors: Racquel Z. LeGeros, New York, NY (US); Haijing Gu, Guangzhou (CN); Dindo Mijares, Woodside, NY (US); Deepak Saxena, New York, NY (US); Sudharani Bodepudi, Piscataway, NJ (US)

(73) Assignee: New York University, New York, NY (US)

( * ) Notice: Subject to any disclaimer, the term of this patent is extended or adjusted under 35 U.S.C. 154(b) by 63 days.

(21) Appl. No.: 13/433,794

(22) Filed: Mar. 29, 2012

(65) Prior Publication Data

US 2012/0315226 A1   Dec. 13, 2012

Related U.S. Application Data

(60) Provisional application No. 61/516,079, filed on Mar. 29, 2011.

(51) Int. Cl.
*A61Q 11/00* (2006.01)
*A61K 8/21* (2006.01)
*A61K 8/27* (2006.01)
*A61K 8/24* (2006.01)
*A61K 6/033* (2006.01)
*A61K 6/04* (2006.01)
*A61K 6/00* (2006.01)

(52) U.S. Cl.
CPC ..................... *A61K 6/0017* (2013.01)

(58) Field of Classification Search
USPC .......................... 424/52, 57, 401, 49; 433/216
See application file for complete search history.

(56) References Cited

U.S. PATENT DOCUMENTS

| | | | | |
|---|---|---|---|---|
| 4,139,599 | A | * | 2/1979 | Tomlinson et al. ............ 423/308 |
| 4,556,561 | A | * | 12/1985 | Brown et al. .................. 424/606 |
| 5,104,644 | A | * | 4/1992 | Douglas ........................ 424/53 |
| 5,266,534 | A | | 11/1993 | Atsumi et al. |
| 5,993,785 | A | * | 11/1999 | Johansen et al. ................ 424/49 |
| 2009/0068285 | A1 | | 3/2009 | LeGeros et al. |

FOREIGN PATENT DOCUMENTS

WO    2007022211    2/2007

OTHER PUBLICATIONS

Daugela, et al., "Antibacterial potential of contemporary dental luting cements", Stomatologija, 2008, 10(1): 16-21.
Addy, et al., "Dentin hypersensitivity: an overview on which to base tubule" J Clin Dent (2010) 21[Spec Iss]: 25-30.
Beignton, et al., "A microbiological study of primary root-caries lesions with different treatment needs" J Dent Res (1993) 72(3):623-9.
Beltran-Aguilar, et al., "Fluoride varnishes. A review of their clinical use, cariostatic mechanism, efficacy and safety" J Am Dent Assoc (2000) 131(5):589-96.
Bowden, et al., "Associate of selective bacteria with the lesions of root surface caries" Oral Microbiol Immunol (1990) 5 (6):346-51.
Brannstrom, et al., "The hydrodynamics of the dentine, its possible relationship to dental pain" Int Dent J (1972) 22:219-227.
Chhour, et al., "Molecular analysis of microbial diversity in advanced caries" J Clin Microbiol (2005) 43(2):843-9.
Chou, et al., "Antibacterial effect of zinc phosphate mineralized guided bone regeneration membranes" Implant Dent (2007) 16(1):89-100.
Daneshmehr, et al., "Effects of root dentin surface coating with all-in-one adhesive materials on biofilm adherence" J Dent 92008) 36(1):33-41.
Drisko, et al., "Dentine Hypersensitivity—dental hygiene and periodontal considerations" Int Dent J (2002) 52:385-393.
Eisenberg, et al., "Interactions of sanguinarine and zinc on oral streptoccoci and Actinomyces species" Caries Res (1991) 25(3): 185-90.
Ellen, et al., "Streptococcus mutans and Lactobacillus detection in the assessment of dental root surface caries risk" J Dent Res (1985) 64(10): 1245-9.
Featherstone, "Fluoride remineralization and root caries" Am J Dent (1994) 7(5): 271-4.
Ganss, et al., "Effect of two fluoridation measures on erosion progression in human enamel and dentine in situ" Caries Res (2004) 38(6):561-6.
Gillam, et al., "The effects of oxalate-containing products on the exposed dentine surface: An SEM investigation" J Am (1990) 34:561-581.
Holland, et al., "Guidelines for the design and conduct of clinical trials on dentine hypersensitivity" J Clin Periodontol (1997) 24:808-813.
Katz, et al., "Prevalence and intraoral distribution of root caries in an adult population" Caries Res (1982) 16(3):265-71.
Keltjens, et al., "Preventive aspects of root caries" Int Den J (1993) 43:143-148.

(Continued)

*Primary Examiner* — Lezah Roberts
(74) *Attorney, Agent, or Firm* — Klauber & Jackson LLC

(57) ABSTRACT

The present invention provides compositions including saturated calcium phosphate (sCaP) solutions, that may be prepared from mixtures of calcium deficient apatite and one or more of sodium fluoride and zinc chloride, or F or Zn ions. The solutions may be prepared from mixtures of calcium compounds and one or more of sodium or potassium phosphates, sodium or potassium fluoride and zinc salts with, for instance, either phosphoric or hydrochloric acids. Such compositions may be useful for increasing occlusion of dentin tubules, decreasing bacterial attachment to dentin tubules, decreasing bacterial growth or colonization on tooth surfaces such as enamel and dentin surfaces including on dentin tubules, increasing resistance to acid dissolution, inhibiting dental caries formation and progression and tooth decay and inhibiting development of tooth hypersensitivity.

11 Claims, 33 Drawing Sheets

(56) References Cited

OTHER PUBLICATIONS

Kishore, et al., "Effectiveness of Desensitizing Agents" Journal of Endodontics (2002) 28(1): 34-35.

LeGeros, "Chemical and crystallographic events in the caries process" J Dent Res 69 Spec (1990) No. (567-74) discussion 634-6.

LeGeros, "Calcium Phosphates in Demineralization/Remineralization Processes" J Clin Dent (1999) X(2):65-73.

Markowitz, "The original desensitizers: strontium and potassium salts" J Clin Dent (2009) 20 (Spec Iss).

Marsh, "Dental plaque as a biofilm and microbial community—implications for health and disease" BMC Oral Health (2006) 6 Suppl. 1(S14).

Moreno, "Role of Ca-P-F in caries prevention: chemical aspects" Int Dent J (1993) 43(1 Suppl 1):71-80.

Pashley, "Mechanisms of dentin sensitvity" Dent Clin North Am (1990) 34:449-473.

Pashley, et al. "The effects of oxalate treatment on the smear layer of ground surfaces of human dentine" Arch Oral Biol (1985) 30:731-737.

Percival, et al "Age-related microbiological changes in the salivary and plaque microflora of healthy adults", J Med Microbiol (1991) 35:5-11.

Petersson, et al., "Remineralization study of artificial root caries lesions after fluoride treatment. An in vitro study using electric caries monitor and transversal micro-radiography" Gerodontology (2004) 21(2):85-92.

Preza, et al., "Bacterial profiles of root caries in elderly patients" J Clin Microbiol (2008) 46(6):2015-21.

Ravald, et al., "Long-term evaluation of root surface caries in periodontally-treated patients" J Clin Periodontol (1986) 13(8):758-67.

Reynolds, "Remineralization of enamel subsurface lesions by casein phosphopeptide-stabilized calcium phosphate solutions" J Dent Res (1997) 76(9):1587-95.

Sanz, et al., "The effect of a dentifrice containing chlorhexidine and zinc on plaque, gingivitis, calculus and tooth staining" J Clin Periodontol (1994) 21(6):431-7.

Schlueter, et al. "Effect of stannous and fluoride concentration in a mouth rinse on erosive tissue loss in enamel in vitro" Arch Oral Biol (2009) 54(5):432-6.

Tagami, et al., "Pulp protection and restoration with adhesive resin" Japanese Adhesive Dentistry (1999) 17(56-60).

Trowbridge, et al., "A review of current approaches to in-office management of tooth hypersensitivity" Dent Clin North Am (1990) 34:561-581.

Van Loveren, et al., Comparison of the effects of fluoride and the ionophore nigericin on acid production by streptococcus mutans and the resultant in vitro enamel demineralization J Dent Res (1987) 66(11): 1658-62C.

van Rijkom, et al., "A meta-analysis of clinical studies on the caries-inhibiting effect of fluoride gel treatment" Caries Res (1998) 32(2):83-92.

Wolff, "Dentin Hypersensitivity the biofilm and remineralization: What is the connection?" Adv Dent Res (2009) 21:21-24.

Zambon, et al., "The microbiology and histopathology of human root caries" Am J Dent (1995) 8(6):323-8.

\* cited by examiner

SE    WD 8.6mm 20.0kV x2.0k 20um

SE    WD 7.8mm 20.0kV x20k 2um

SE　　　　WD 8.1mm 20.0kV x20k 2um

SE　　　　WD 8.0mm 20.0kV x20k 2um

SE　　　　WD 8.7mm 20.0kV x20k 2um

SE　　　　WD 8.1mm 20.0kV x20k 2um

WD 8.8mm 20.0kV x5.0k 10um

SE  WD 8.5mm 20.0kV x5.0k 10um

SE  WD 9.5mm 15.0kV x5.0k 10um

WD 8.5mm 20.0kV x5.0k 10um

SE  WD 8.1mm 20.0kV x20k 2um

SE  WD 7.6mm 20.0kV x20k 2um

SE  WD 8.0mm 20.0kV x20k 2um

SE  WD 8.7mm 20.0kV x20k 2um

SE  WD 8.7mm 20.0kV x20k 2um

SE  WD 7.8mm 20.0kV x20k 2um

SE  WD 8.1mm 20.0kV x20k 2um

SE  WD 8.6mm 20.0kV x20k 2um

After immersion in KAc for 30min

SE    WD 8.4mm 20.0kV x2.0k 20um

SE    WD 8.8mm 20.0kV x20k 2um

SE    WD 8.7mm 20.0kV x2.0k 20um

SE    WD 8.0mm 20.0kV x20k 2um

SE    WD 7.7mm 20.0kV x2.0k 20um

SE    WD 8.0mm 20.0kV x18k 2um

SE    WD 8.6mm 20.0kV x2.0k 20um

SE    WD 8.6mm 20.0kV x20k 2um

SE   WD 8.7mm 20.0kV x1.0k 50um

SE   WD 8.6mm 20.0kV x1.0k 50um

SE   WD 8.6mm 20.0kV x6.0k 5um

SE   WD 8.6mm 20.0kV x6.0k 5um

SE   WD 8.6mm 20.0kV x10k 5um

SE   WD 8.6mm 20.0kV x10k 5um

SE   WD 8.6mm 20.0kV x2.0k 20um

SE   WD 8.2mm 20.0kV x2.0k 20um

SE       WD 5.5mm 20.0kV x2.0k 20um

SE　　　　　WD 5.9mm 20.0kV x10k 5um

SE　　　　　WD 6.4mm 20.0kV x10k 5um

SE    WD 6.8mm 10.0kV x10k 5um

SE    WD 6.8mm 10.0kV x10k 5um

SE  WD 7.4mm 10.0kV x10k 5um

SE  WD 7.1mm 10.0kV x10k 5um

ANTI-BACTERIAL AND MINERALIZING CALCIUM PHOSPHATE COMPOSITIONS

This application claims priority to U.S. provisional patent application Ser. No. 61/516,079, filed on Mar. 29, 2011, the disclosure of which is herein incorporated by reference in its entirety.

FIELD OF THE INVENTION

The present invention relates generally to methods for and compositions useful for modifying the dentin and enamel surfaces of teeth thus promoting occlusion of dentinal tubules, increasing the resistance of the dentin and enamel surfaces and the dentin tubule precipitates to acid dissolution and preventing or minimizing adherence and colonization of oral bacteria to tooth surfaces.

BACKGROUND OF THE INVENTION

The population of the elderly is increasing worldwide. Due to better dental health care, the elderly are retaining their teeth longer. Receding gum line with age results in exposed root dentin that becomes susceptible to dentin hypersensitivity (DH) and root caries formation—two major concerns in oral health. (Keltjens, et al., Int Dent J (1993) 43: 143-148; Percival, et al., J Med Microbiol (1991) 35: 5-11) In addition, DH is experienced by as high as 57% of young and old population (Drisko, et al., Int Dent J (2002) 52: 385-393) with exposed dentin that may have been caused by erosion (e.g., due to external acids from food or drink), abrasion (due to excessive or improper tooth brushing), aging (gum recession), or periodontal treatment.

The accepted definition of dentin hypersensitivity (DH) is that "it is characterized by short sharp pain arising from exposed dentin in response to stimuli, typically thermal, evaporative, tactile, osmotic or chemical and which cannot be ascribed to any other form of dental defect or pathology". (Holland, et al., J Clin Periodontol (1997) 24: 808-813) The hydrodynamic mechanism for DH first proposed by Gysi and expanded by Brannstrlm et al in 1972 and Pashley in 1990, stated that an stimulus applied to exposed dentin cause an increase in the rate of fluid flow in the dentinal tubules "causing a hydrodynamic pressure change across dentin, activating the pulpal nerve fibers and evoking pain". (Gysi, Br J Dent Sci (1900) 43: 865-868, Brannstrom, et al., Int Dent J (1972) 22: 219-227; Pashley, Dent Clin North Am (1990); 34: 449-473; Addy, et al., J Clin Dent (2010); 21[Spec Iss]: 25-30) The intensity of dentin hypersensitivity has been associated with the number and width of exposed tubules. (Pashley, et al., Arch Oral Biol (1985); 30: 731-737) Strategies to treat dentin hypersensitivity have included chemical or physical means of blocking or modifying pulpal nerve response to external stimuli, and/or occluding dentinal tubules to stop or reduce the fluid flow across dentin. (Addy, et al., J Clin Dent (2010); 21 [Spec Iss]: 25-30) Desensitizing agents to block pulpal nerve response include treatments with potassium and stannous salts or the more recently introduced arginine-containing desensitizing agent. (Markowitz, J Clin Dent (2009); 20 (spec Iss); Wolff, Adv Dent Res (2009); 21: 21-24) Agents that occlude dentinal tubules by forming precipitates have included: use of strontium chloride and sodium fluoride, potassium nitrate and potassium oxalate, dentin bonding agents. (Kishore, et al., J Endod (2002); 28: 34-35; Gillam, et al. J Oral Rehabil (2001); 28: 1037-1044; Trowbridge, et al., Dent Clin North Am (1990); 34: 561-581)

It would be desirable to provide a treatment in modifying the dentin surface by promoting occlusion of dentinal tubules and increasing the resistance of the dentin surface and the dentin tubule precipitates to acid dissolution. Since dentin tubule occlusion is associated with dentin hypersensitivity, such a treatment may have the potential of minimizing dentin hypersensitivity by occluding dentin tubules with precipitates that are less susceptible to acid dissolution.

Enamel and dentin caries are initiated by the dissolution or demineralization of the enamel or dentin mineral by acids produced by oral bacteria. In the case of dentin caries, the fermentation of the food carbohydrates by the oral bacteria produces acid that initiates the caries process, i.e., dissolution of the dentin mineral followed by the breaking down of the organic matrix (primarily, collagen) by the bacterial enzymes (Featherstone, Am J Dent (1994) 7(5):271-4; Zambon, et al, Am J Dent (1995) 8(6):323-8).

Earlier culture-based (Bowden, et al., Oral Microbiol Immunol (1990) 5(6):346-51; Ellen, et al., J Dent Res (1985) 64(10):1245-9) and more recent culture-independent studies (Chhour, et al., J Clin Microbiol (2005) 43(2):843-9; Preza, et al., J Clin Microbiol (2008) 46(6):2015-21) have shown that Streptococcus mutans and lactobacilli are the principal microorganisms associated with root caries.

Root caries has become a significant oral health issue. Periodontal disease or its treatment leads to gingival recession resulting in the exposure of the root surfaces supragingivally (Katz, et al., Caries Res (1982) 16(3):265-71; Ravald, et al., J Clin Periodontol (1986) 13(8):758-67) that become susceptible to caries development. According to epidemiologic studies, root caries especially among the middle aged and the elderly, is prevalent among patients with treated and untreated periodontal disease.

Current therapies to prevent or arrest dentin or root caries through remineralization process include: mouth rinses (Schlueter, et al., Arch Oral Biol (2009) 54(5):432-6), fluoridated dentifrices (Ganss, et al., Caries Res (2004) 38(6):561-6), varnishes (Beltran-Aguilar, et al., J Am Dent Assoc (2000) 131(5):589-96) and gels (van Rijkom, et al., Caries Res (1998) 32(2):83-92) and calcium phosphate remineralizing solutions. (Reynolds, J Dent Res (1997) 76(9):1587-95).

The presence of fluoride ($F^-$) ions increases the mineralizing efficiency of the CaP solutions and inhibits enamel dissolution by the formation of less soluble fluoridated hydroxyapatite (LeGeros, J Dent Res 69 Spec (1990) No (567-74; discussion 634-6; LeGeros, J Clin Dent (1999) X(2):65-73; Moreno, Int Dent J (1993) 43(1 Suppl 1):71-80). In addition, $F^-$ ions reduce the metabolism of oral bacteria. (Van Loveren, et al., J Dent Res (1987) 66(11):1658-62C) Prevention of the adherence of cariogenic bacteria to tooth surfaces is considered to be an important strategy for controlling dental caries (Marsh, BMC Oral Health (2006) 6 Suppl. 1 (S14)). It was reported that a barrier-like film layer plays an important role in protecting dentin from physical, chemical and biological stimuli (Tagami, et al., Japanese Adhesive Dentistry, (1999) 17(56-60)). All-in-one adhesives (a fluoride-releasing adhesive) coated on the root dentin can inhibit Streptococcus mutans biofilm formation through a protective layer covering exposed root dentinal surfaces. (Daneshmehr, et al., J Dent (2008) 36(1): 33-41)

Because root caries is a plaque-related disease associated with specific microorganisms (Beighton, et al., J Dent Res (1993) 72(3):623-9), mineralizing agents combined with mechanical and/or chemical treatments to control bacterial plaque are necessary for preventing and arresting root caries (Petersson, et al., Gerodontology (2004) 21(2):85-92).

Zinc ($Zn^{2+}$) ions released from zinc salts have been shown to provide antibacterial property, inhibiting plaque formation and gingival inflammation (Eisenberg, et al., *Caries Res* (1991) 25(3):185-90; (Sanz, et al., *J Clin Periodontol* (1994) 21(6):431-7). Our previous studies showed that polymer membranes (such as those used for guided bone regeneration) when mineralized with zinc-containing calcium phosphate compound, inhibited the growth and colonization of oral bacteria (Chou, et al., *Implant Dent* (2007) 16(1):89-100). Another study demonstrated that Zn-releasing calcium phosphate compounds deposited on orthodontic brackets also inhibited in vitro bacterial growth and development (Park, et al., *J Dent Res* (2005) 84 (1917). It would be beneficial to provide solutions for increasing resistance to acid dissolution and in inhibiting the adherence and colonization of cariogenic organisms such as *Streptococcus mutans* on dentin surfaces.

SUMMARY OF THE INVENTION

The present invention is based in part upon the discovery that compositions including saturated calcium phosphate (sCaP) solutions, some having a pH ranging from 5 to 7.0, that may be prepared from mixtures of calcium deficient apatite (prepared by precipitation), and optionally one or more of sodium fluoride and zinc chloride may be useful for one or more of increasing occlusion of dentin tubules, decreasing bacterial attachment to dentin tubules, decreasing bacterial growth or colonization on tooth (e.g., enamel or dentin) surfaces including on dentin tubules, inhibiting tooth decay, inhibiting solubility of a tooth (e.g. enamel or dentin) or inhibiting development of tooth hypersensitivity. The saturated calcium phosphate sCaP solutions may also be prepared from, for instance, mixtures of calcium salts (e.g., calcium carbonate, calcium fluoride) and phosphoric acid or sodium or potassium phosphates and sodium or potassium fluoride with or without zinc salts. Also, the saturated calcium phosphate sCaP solutions may be prepared from mixtures of calcium phosphates (DCPD, OCP, TCP) with sodium or potassium sodium or potassium fluoride with or without zinc salts in, for instance, a dilute hydrochloric solution. Further, the sCaP solutions may also be prepared from mixtures of calcium compounds and sodium or potassium oxalates, sodium or potassium phosphates and sodium or potassium fluoride with or without zinc salts. In many instances, the solutions are supersaturated with respect to F- or Zn-substituted calcium phosphates, and in many instances, the solutions are supersaturated with both F- and Zn-substituted calcium phosphates.

In a first aspect, the invention provides methods for of increasing or promoting occlusion of dentin tubules on the surface of teeth. The methods feature providing a composition including calcium and optionally one or more of fluoride or zinc, such as a saturated calcium phosphate (sCaP) solution and optionally one or more of fluoride or zinc. The calcium phosphate (sCaP) solution may be prepared from mixtures of a calcium source such as calcium carbonate or calcium deficient apatite, prepared for instance, by precipitation, and optionally one or more of sodium fluoride and zinc chloride. In many instances, the solutions are supersaturated with respect to F- or Zn-substituted calcium phosphates, and in many instances, the solutions are supersaturated with both F- and Zn-substituted calcium phosphates. Exemplary solutions may be prepared by mixing a fluoride source with a calcium deficient apatite in weight ratios of about 1:2, 1:4, 1:5, 1:10, 1:25, 1:50 or so. Optionally, a zinc source may be provided in about the same weight ratio as the fluoride source or the zinc source may be provided in weight ratios with respect to the calcium deficient apatite of 1:2, 1:4, 1:5, 1:10, 1:25, 1:50, 1:75, 1:100 or so. The fluoride source may be sodium fluoride and the zinc source may be zinc chloride. The calcium deficient apatite, the fluoride source and optionally the zinc source may be mixed in an acidic solution such as, for instance, a solution containing $H_3PO_4$ in volumes of, for instance, 1% to 25%, 2% to 15%, 3% to 10%, or about 4%, 5% or 6%. In many instances the solutions have a pH of about 3.0 to 9.0, preferably 4.0 to 8.0, in many instances 5.0 to 7.5, sometimes 5.5 to 7.0. The composition or solution is provided so as to contact the surface of teeth containing dentin tubules. The composition or solution may be provided in the form of an oral rinse or a mouthwash or a gel preparation, for instance. The composition or solution may be provided in contact with the tooth, for example, the enamel, dentin, or root dentin surface for a period of about, for instance, 10 seconds, 20 seconds, 30 seconds, 1 minute, 2 minutes, 3 minutes, 4 minutes, 5 minutes, 10 minutes, 15 minutes, 20 minutes, 30 minutes, or an hour or more. The methods may result in substantial occlusion of 10%, 20%, 30%, 40%, 50%, 55%, 60%, 65%, 70%, 75%, 80%, 85%, 90%, 95%, or more including substantially all of dentin tubules present on the tooth surface. The methods may also result in a mean occlusion of 10%, 20%, 30%, 40%, 50%, 55%, 60%, 65%, 70%, 75%, 80%, 85%, 90%, 95%, or more including substantially all of all the dentin tubules present on the tooth surface. The methods may be performed ex vivo or in vivo in a biological subject such as, for instance, a mammal such as a human.

In a second aspect, the present invention provides methods for decreasing bacterial attachment to dentin tubules or decreasing bacterial attachment to the surface of teeth. The methods feature providing a composition including calcium and optionally one or more of fluoride or zinc, such as a saturated calcium phosphate (sCaP) solution and optionally one or more of fluoride or zinc. The calcium phosphate (sCaP) solution may be prepared from mixtures of calcium deficient apatite, prepared for instance, by precipitation, and optionally one or more of sodium fluoride and zinc chloride. In many instances, the solutions are supersaturated with respect to F- or Zn-substituted calcium phosphates, and in many instances, the solutions are supersaturated with both F- and Zn-substituted calcium phosphates. Exemplary solutions may be prepared by mixing a fluoride source with a calcium deficient apatite in weight ratios of about 1:2, 1:4, 1:5, 1:10, 1:25, 1:50 or so. Optionally, a zinc source may be provided in about the same weight ratio as the fluoride source or the zinc source may be provided in weight ratios with respect to the calcium deficient apatite of 1:2, 1:4, 1:5, 1:10, 1:25, 1:50, 1:75, 1:100 or so. The fluoride source may be sodium fluoride and the zinc source may be zinc chloride. The calcium deficient apatite, the fluoride source and optionally the zinc source may be mixed in an acidic solution such as, for instance, a solution containing $H_3PO_4$ in volumes of, for instance, 1% to 25%, 2% to 15%, 3% to 10%, or about 4%, 5% or 6%. In many instances the solutions have a pH of about 3.0 to 9.0, preferably 4.0 to 8.0, in many instances 5.0 to 7.5, sometimes 5.5 to 7.0. The composition or solution is provided so as to contact the surface of a tooth containing dentin tubules. The composition or solution may be provided in the form of an oral rinse or a mouthwash or a gel preparation, for instance. The composition or solution may be provided in contact with the surface of teeth containing dentin tubules for a period of about, for instance, 10 seconds, 20 seconds, 30 seconds, 1 minute, 2 minutes, 3 minutes, 4 minutes, 5 minutes, 10 minutes, 15 minutes, 20 minutes, 30 minutes, or an hour or more. The methods may result in a decrease in the number of bacteria attached to the tooth surface or to the surface of a dentin tubule of 10%, 20%, 30%, 40%, 50%, 55%, 60%, 65%, 70%, 75%, 80%, 85%, 90%, 95%, or more including substantially no attachment of bacteria to the tooth surface, as compared to controls. The methods may be performed ex vivo or in vivo in a biological subject such as, for instance, a mammal such as a human. The methods may be effective with a large number or all bacteria, such as, for instance, *Streptococcus mutans*.

In a third aspect, the present invention provides methods for decreasing bacterial growth or colonization on the surface of a tooth, for instance, the enamel, dentin, or root dentin surface. The methods feature providing a composition including calcium and optionally one or more of fluoride or zinc, such as a saturated calcium phosphate (sCaP) solution and optionally one or more of fluoride or zinc. The calcium phosphate (sCaP) solution may be prepared from mixtures of calcium deficient apatite, prepared for instance, by precipitation, and optionally one or more of sodium fluoride and zinc chloride. In many instances, the solutions are supersaturated with respect to F- or Zn-substituted calcium phosphates, and in many instances, the solutions are supersaturated with both F- and Zn-substituted calcium phosphates. Exemplary solutions may be prepared by mixing a fluoride source with a calcium deficient apatite in weight ratios of about 1:2, 1:4, 1:5, 1:10, 1:25, 1:50 or so. Optionally, a zinc source may be provided in about the same weight ratio as the fluoride source or the zinc source may be provided in weight ratios with respect to the calcium deficient apatite of 1:2, 1:4, 1:5, 1:10, 1:25, 1:50, 1:75, 1:100 or so. The fluoride source may be sodium fluoride and the zinc source may be zinc chloride. The calcium deficient apatite, the fluoride source and optionally the zinc source may be mixed in an acidic solution such as, for instance, a solution containing $H_3PO_4$ in volumes of, for instance, 1% to 25%, 2% to 15%, 3% to 10%, or about 4%, 5% or 6%. In many instances the solutions have a pH of about 3.0 to 9.0, preferably 4.0 to 8.0, in many instances 5.0 to 7.5, sometimes 5.5 to 7.0. The composition or solution is provided so as to contact the surface of teeth containing dentin tubules. The composition or solution may be provided in the form of an oral rinse or a mouthwash or a gel preparation, for instance. The composition or solution may be provided in contact with the surface of teeth containing dentin tubules for a period of about, for instance, 10 seconds, 20 seconds, 30 seconds, 1 minute, 2 minutes, 3 minutes, 4 minutes, 5 minutes, 10 minutes, 15 minutes, 20 minutes, 30 minutes, or an hour or more. The methods may result in a decrease in the speed of growth of bacteria or expansion of bacterial colonies attached to the tooth surface or to the surface of a dentin tubule of 10%, 20%, 30%, 40%, 50%, 55%, 60%, 65%, 70%, 75%, 80%, 85%, 90%, 95%, or more including substantially no bacteria growth or no expansion of bacterial colonies on the tooth surface, as compared to controls. The methods may be performed ex vivo or in vivo in a biological subject such as, for instance, a mammal such as a human. The methods may be effective with a large number or all bacteria, such as, for instance, *Streptococcus mutans*.

In a fourth aspect, the present invention provides methods for inhibiting tooth decay including inhibiting tooth solubility, for instance, inhibiting enamel solubility or inhibiting development of tooth hypersensitivity. The methods feature providing a composition including calcium and optionally one or more of fluoride or zinc, such as a saturated calcium phosphate (sCaP) solution and optionally one or more of fluoride or zinc. The calcium phosphate (sCaP) solutions may be prepared from mixtures of calcium deficient apatite, prepared for instance, by precipitation, and optionally one or more of sodium fluoride and zinc chloride. In many instances, the solutions are supersaturated with respect to F- or Zn-substituted calcium phosphates, and in many instances, the solutions are supersaturated with both F- and Zn-substituted calcium phosphates. Exemplary solutions may be prepared by mixing a fluoride source with a calcium deficient apatite in weight ratios of about 1:2, 1:4, 1:5, 1:10, 1:25, 1:50 or so. Optionally, a zinc source may be provided in about the same weight ratio as the fluoride source or the zinc source may be provided in weight ratios with respect to the calcium deficient apatite of 1:2, 1:4, 1:5, 1:10, 1:25, 1:50, 1:75, 1:100 or so. The fluoride source may be sodium fluoride and the zinc source may be zinc chloride. The calcium deficient apatite, the fluoride source and optionally the zinc source may be mixed in an acidic solution such as, for instance, a solution containing $H_3PO_4$ in volumes of, for instance, 1% to 25%, 2% to 15%, 3% to 10%, or about 4%, 5% or 6%. In many instances the solutions have a pH of about 3.0 to 9.0, preferably 4.0 to 8.0, in many instances 5.0 to 7.5, sometimes 5.5 to 7.0. The composition or solution is provided so as to contact the surface of teeth containing dentin tubules. The composition or solution may be provided in the form of an oral rinse or a mouthwash or a gel preparation, for instance. The composition or solution may be provided in contact with the surface of teeth containing dentin tubules for a period of about, for instance, 10 seconds, 20 seconds, 30 seconds, 1 minute, 2 minutes, 3 minutes, 4 minutes, 5 minutes, 10 minutes, 15 minutes, 20 minutes, 30 minutes, or an hour or more. The methods may result in a decrease in the rate of tooth decay or the rate of developing hypersensitivity in a tooth of 10%, 20%, 30%, 40%, 50%, 55%, 60%, 65%, 70%, 75%, 80%, 85%, 90%, 95%, or more including substantially no tooth decay or no development of hypersensitivity in a tooth, as compared to controls. The methods may be performed ex vivo or in vivo in a biological subject such as, for instance, a mammal such as a human.

In a fifth aspect, the present invention provides methods for inhibiting acid dissolution of a tooth surface. The methods feature providing a composition including calcium and optionally one or more of fluoride or zinc, such as a saturated calcium phosphate (sCaP) solution and optionally one or more of fluoride or zinc. The calcium phosphate (sCaP) solutions may be prepared from mixtures of calcium deficient apatite, prepared for instance, by precipitation, and optionally one or more of sodium fluoride and zinc chloride. In many instances, the solutions are supersaturated with respect to F- or Zn-substituted calcium phosphates, and in many instances, the solutions are supersaturated with both F- and Zn-substituted calcium phosphates. Exemplary solutions may be prepared by mixing a fluoride source with a calcium deficient apatite in weight ratios of about 1:2, 1:4, 1:5, 1:10, 1:25, 1:50 or so. Optionally, a zinc source may be provided in about the same weight ratio as the fluoride source or the zinc source may be provided in weight ratios with respect to the calcium deficient apatite of 1:2, 1:4, 1:5, 1:10, 1:25, 1:50, 1:75, 1:100 or so. The fluoride source may be sodium fluoride and the zinc source may be zinc chloride. The calcium deficient apatite, the fluoride source and optionally the zinc source may be mixed in an acidic solution such as, for instance, a solution containing $H_3PO_4$ in volumes of, for instance, 1% to 25%, 2% to 15%, 3% to 10%, or about 4%, 5% or 6%. In many instances the solutions have a pH of about 3.0 to 9.0, preferably 4.0 to 8.0, in many instances 5.0 to 7.5, sometimes 5.5 to 7.0. The composition or solution is provided so as to contact the surface of teeth containing dentin tubules. The composition or solution may be provided in the form of an oral rinse or a mouthwash or a gel preparation, for instance. The composition or solution may be provided in contact with the surface of teeth containing dentin tubules for a period of about, for instance, 10 seconds, 20 seconds, 30 seconds, 1 minute, 2 minutes, 3 minutes, 4 minutes, 5 minutes, 10 minutes, 15 minutes, 20 minutes, 30 minutes, or an hour or more. The methods may result in a decrease in the rate of acid dissolution of a tooth surface or of the absolute amount of acid dissolution of a tooth surface over a fixed period of time of 10%, 20%, 30%, 40%, 50%, 55%, 60%, 65%, 70%, 75%, 80%, 85%, 90%, 95%, or more including substantially no acid dissolution of a tooth surface over a given period of time, as compared to controls. The methods may be performed ex vivo or in vivo in a biological subject such as, for instance, a mammal such as a human.

In a sixth aspect, the present invention provides compositions that may be useful for one or more of increasing occlusion of dentin tubules, decreasing bacterial attachment to dentin tubules, decreasing bacterial growth or colonization on tooth surfaces including on dentin tubules, inhibiting tooth decay or inhibiting development of tooth hypersensitivity. The compositions include calcium and optionally one or more of fluoride or zinc, such as a saturated calcium phosphate (sCaP) solution and optionally one or more of fluoride or zinc. These calcium phosphate (sCaP) solutions may be prepared from mixtures of calcium deficient apatite (prepared by precipitation), and optionally one or more of sodium fluoride and zinc chloride. These solutions may also be prepared using any calcium compounds such as calcium carbonate mixed with one or more of fluoride or zinc salts in acidic phosphate solutions. Also, these solutions may be prepared by using calcium phosphate compounds such as one or more of dicalcium phosphate dehydrate, dicalcium phosphate anhydrous, tricalcium phosphate, and amorphous calcium phosphate mixed with one or more of fluoride or zinc salts in acidic solutions. In many instances, the solutions are supersaturated with respect to F- or Zn-substituted calcium phosphates, and in many instances, the solutions are supersaturated with both F- and Zn-substituted calcium phosphates. Exemplary solutions may be prepared by mixing a fluoride source with a calcium deficient apatite in weight ratios of about 1:2, 1:4, 1:5, 1:10, 1:25, 1:50 or so. Optionally, a zinc source may be provided in about the same weight ratio as the fluoride source or the zinc source may be provided in weight ratios with respect to the calcium deficient apatite of 1:2, 1:4, 1:5, 1:10, 1:25, 1:50, 1:75, 1:100 or so. The fluoride source may be sodium fluoride and the zinc source may be zinc chloride. The calcium deficient apatite, the fluoride source and optionally the zinc source may be mixed in an acidic solution such as, for instance, a solution containing $H_3PO_4$ in volumes of, for instance, 1% to 25%, 2% to 15%, 3% to 10%, or about 4%, 5% or 6%. In many instances the solutions have a pH of about 3.0 to 9.0, preferably 4.0 to 8.0, in many instances 5.0 to 7.5, sometimes 5.5 to 7.0. The composition or solution may be provided in the form of an oral rinse or a mouthwash or a gel preparation, for instance.

BRIEF DESCRIPTION OF THE DRAWINGS

FIG. 19 provides microCT images of early enamel caries before and after 14-day treatment with a sCaP solution as described herein showing repair of the caries lesion.

DETAILED DESCRIPTION OF THE INVENTION

Figure 1:
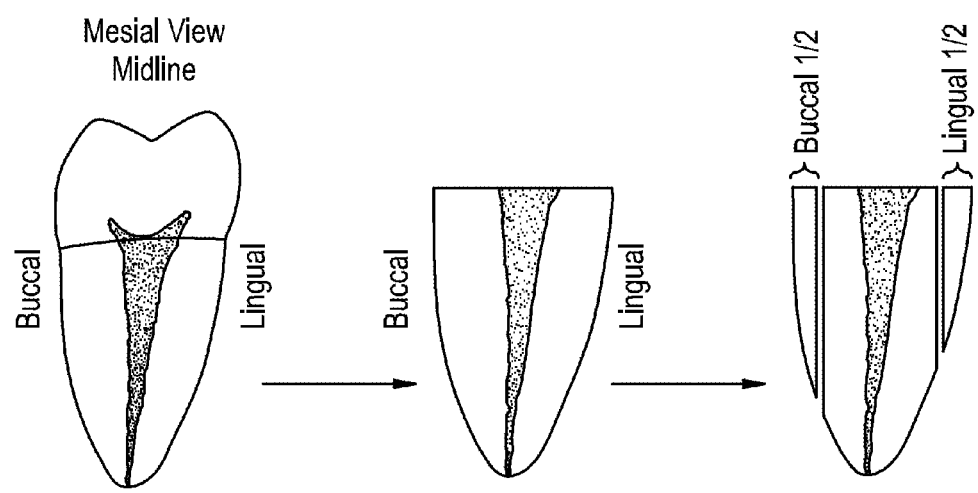
FIG. 1 is a diagram showing the architecture of the tooth including the long axis of the root and the root divided in the mesio-distal direction to obtain buccal 1/2nd or lingual 1/2nd dentin sections.

Various terms used in the specification are defined as follows:

In a specific embodiment, the term "about" means within 20%, preferably within 10%, and more preferably within 5%.

An "effective amount" is an amount that when administered is effective to increase occlusion of dentin tubules, decrease bacterial attachment to dentin tubules, decrease bacterial growth or colonization on tooth surfaces including on dentin tubules, inhibit tooth decay or inhibit development of tooth hypersensitivity.

The term "topical solution or suspension" or "oral solution or suspension" means a solution or suspension that can be administered to the external surface of an affected oral area. The solution or suspension may contain coloring or flavoring as needed to increase patient acceptance. It may be administered in the form of a lozenge, lollipop, pellet, cream, gel, ointment, quick dissolving tablet, gum, mucosal adhesive, or any other solid form that will permit contact of the azathioprine with the oral mucosal surfaces as well as in the form of an oral rinse or mouthwash.

By "pharmaceutically acceptable", is meant is that the carrier or salt is compatible with the other components of the solution or suspension and is not deleterious or harmful to the patient.

Treatment of dentin sections with calcium phosphate-based solutions results in (a) deposition of a coating; (b) occlusion of dentin tubules and (c) increase in resistance to acid dissolution. The amount of the coating and percent of dentin tubule occlusion depends on the pH and concentration of the calcium phosphate-based treatment solutions.

Compared with treatment with oxalate solutions (OX/Ca and OX/P), treatment with solution A3 showed the highest percent of occluded tubules and the higher percent of remaining occluded tubules after exposure to the acidic buffer.

Mineralizing Solutions

The use of calcium phosphate compounds for mineralization of enamel and dentin for caries treatment or prevention has been reported by many authors. (Skrtic, et al., *J Dent Res* (1996) 75: 1679-168) Calcium phosphates such as dicalcium phosphate dihydrate (DCPD) or amorphous calcium phosphate (ACP) with or without fluoride, included in commercial dentifrices or calcium phosphate included in chewing gum are claimed to prevent dental caries. (Itthagarun, et al. *Caries Res* (2005) 39: 251-254; Reynolds, et al., *J Dent Res* (2003) 82: 206-211) Calcifying solutions have been reported to promote mineralization of natural or artificial caries lesion. (Collys, et al. *Caries Res* (1993) 27: 15-20) The use solution containing calcium and phosphate ions for dentinal tubule occlusion has also been reported. (Suge, et al. *Dent Mater J* (2005) 24: 522-529; Suge, et al. *J Dent Res* (1995) 74: 1079-1085)

The solutions according to the present invention contain calcium, phosphate and fluoride ions of different concentrations and different pH (neutral or acidic). These solutions, when administered, result in deposition of a coating that provides changes in surface morphology (from SEM images), difference in crystallite size (from X-ray diffraction analyses), difference in the organic/inorganic ratio from materials scraped from untreated compared to treated dentin surfaces (from FTIR analyses) and difference in dissolution properties between the untreated and treated dentin surfaces. The material deposited was identified as an apatitic material using x-ray diffraction and FTIR analyses. Exemplary solutions may be prepared by mixing a fluoride source with a calcium deficient apatite in weight ratios of about 1:2, 1:4, 1:5, 1:10, 1:25, 1:50 or so. Optionally, a zinc source may be provided in about the same weight ratio as the fluoride source or the zinc source may be provided in weight ratios with respect to the calcium deficient apatite of 1:2, 1:4, 1:5, 1:10, 1:25, 1:50, 1:75, 1:100 or so. The fluoride source may be sodium fluoride and the zinc source may be zinc chloride. The calcium deficient apatite, the fluoride source and optionally the zinc source may be mixed in an acidic solution such as, for instance, a solution containing $H_3PO_4$ in volumes of, for instance, 1% to 25%, 2% to 15%, 3% to 10%, or about 4%, 5% or 6%. In many instances the solutions have a pH of about 3.0 to 9.0, preferably 4.0 to 8.0, in many instances 5.0 to 7.5, sometimes 5.5 to 7.0. Some exemplary solutions that may be useful include, for instance, 1 g calcium deficient apatite (CDA)+20 mg NaF+10 mg $ZnCl_2$ in 10 ml 4.25% $H_3PO_4$, pH adjusted to 7 with NaOH; 1 g calcium deficient apatite (CDA)+20 mg NaF+10 mg $ZnCl_2$ in 10 ml 4.25% $H_3PO_4$, pH adjusted to 5.5 with NaOH; 1 g calcium deficient apatite (CDA)+40 mg NaF+20 mg $ZnCl_2$ in 10 ml 4.25% $H_3PO_4$, pH adjusted to 5.5 with NaOH; 1 g calcium deficient apatite (CDA)+40 mg NaF in 10 ml 4.25% $H_3PO_4$, pH adjusted to 5.5 with NaOH; 2 g calcium deficient apatite (CDA)+500 mg NaF in 10 ml 8.5% $H_3PO_4$, and 1 g $Ca(OH)_2$+200 to 500 mg NaF in 10 ml 4.5 to 8.5% $H_3PO_4$.

These results also demonstrate that the amount of deposits on the dentin surface depends on the pH. Thus, a greater amount of crystals formed on the dentin surfaces treated with solution A2 (pH 5.5) compared to that treated with solution A1 (pH 7.4) even though the composition of both solutions was similar (FIG. 3C compared to FIG. 3B). The greater amount of deposits obtained from solutions with lower pH (A2 vs A1) may be due to dissolution/reprecipitation processes. The dentin mineral (a carbonate apatite) on the dentin surface was partially dissolved releasing $Ca^{2+}$, $Mg^{2+}$, $HPO_4^{1-}$, $CO_3^{2-}$ ions which combined with the $Ca^{2+}$, $Zn^{2+}$, $HPO_4^{1-}$, $F^{1-}$ ions from the treatment solutions to form an apatitic precipitate that had lower $CO_3^{2-}$ ion concentration and higher $F^{1-}$ ion concentration. Such precipitate has lower solubility than the original dentin mineral which had a higher $CO_3^{2-}$ ion concentration and much lower $F^{1-}$ ion concentration. (LeGeros, *J Dent Res* (1990) 69 Spec No: 567-574; discussion 634-566; LeGeros, *Monogr Oral Sci* (1991) 15: 1-201)

Fluoride Effect

Figure 7A:
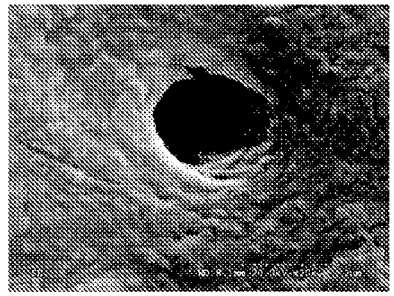
FIG. 7 provides SEM images of dentin surfaces after exposure to acidic buffer for one hour demonstrating an increase in the dentin tubule diameters (FIG. 7). However, the diameter of the dentin tubules of the treated dentin were still smaller compared to those of the control (FIG. 7D, 7F, 7H compared to FIG. 7B) similar to the difference observed before exposure to acid (FIG. 7C, 7E, 7G compared to FIG. 7A). In addition, erosion of the walls of the dentin tubules of the control dentin (FIG. 7B) was observed but not of the treated dentin after exposure to the acidic buffer (FIG. 7D, 7F, 7H). Some deposits remained on the dentin surfaces treated with solutions A2 (FIG. 7F compared with 7E) or A3 (FIG. 7H compared with 7G) even after exposure to the acidic buffer.
Figure 7B:
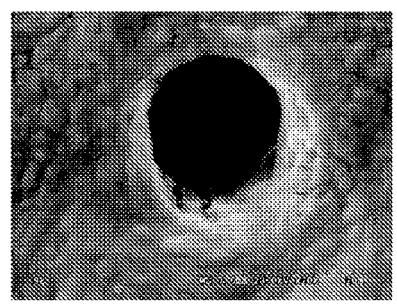
Figure 7C:
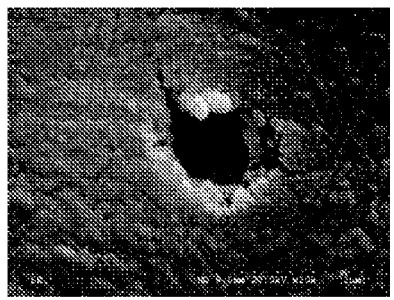
Figure 7D:
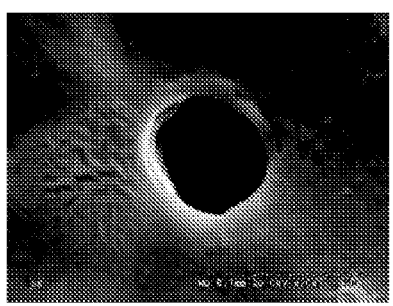
Figure 7E:
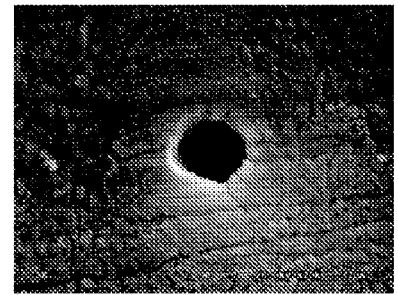
Figure 7F:
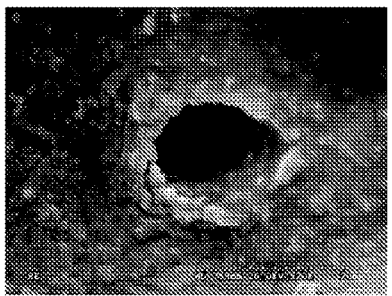
Figure 7G:
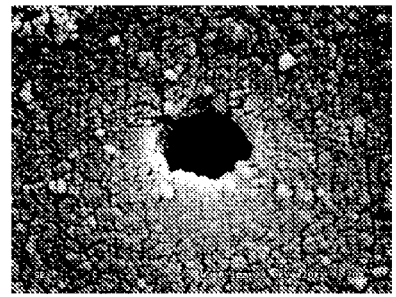
Figure 7H:
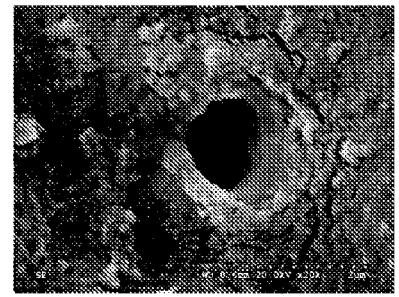

The $F^-$ ion concentration in the mineralizing solution also affects the amount of deposits on the treated surfaces. Higher F concentrations in solution A3 compared to A2 results in greater amount of deposits on the treated surfaces before and after exposure to acidic buffer (FIG. 7D compared to FIG. 7C; FIG. 7H compared to 7F).

Fourier transform infrared spectroscopy shows that increasing the F concentration in apatite causes an increase in the resolution of the P—O (for $PO_4$) absorption band ($v_3$P—O) at 1102, 1065, 1027 cm$^{-1}$. This increase in the resolution of the absorption bands observed for fluoride-containing apatite is due to increase in crystal size and crystal perfection of the apatite.

The lower amount of Ca ions released for deposits from solutions of low pH and higher F concentrations can be attributed to the known effect of fluoride on the properties of apatite. Incorporation of F has been shown to increase the crystal size and decrease the solubility of synthetic and biologic apatites. (LeGeros, *Monogr Oral Sci* (1991) 15: 1-201; LeGeros, et al. in Menczel J, Robin G C, Making M (eds): Osteoporosis. New York, Wiley (1982): 327-341) Studies of in vitro caries lesion formation and progression in shark enameloid (carbonate fluorapatite) compared to that in human enamel (carbonate hydroxyapatite) demonstrate that lesion progression is less, and the extent of remineralization is greater in shark enameloid, and this is attributed to the release of F ions during the dissolution of the shark enameloid mineral (an F-containing carbonate apatite) that subsequently promote the remineralization of the enameloid. (LeGeros, *J Dent Res* (1983) 62: 138-144) Similar observations were made in situ caries formation in enamel treated with F-containing mouth rinses or varnishes. (Sonju Clasen, et al. *Adv*

Dent Res (1997) 11: 442-447) Incorporation of F in the enamel mineral is explained by a process of dissolution (demineralization) and reprecipitation (remineralization) of a more acid resistant F-containing apatite. (LeGeros, *J Dent Res* (1983) 62: 138-144; Tanaka, et al., *Arch Oral Biol* (1993); 38: 863-869) Furthermore, dissolution of F-containing apatite increases the F-concentration in the solution surrounding the dentin facilitating remineralization. The presence of F− in solution was shown to inhibit the dissolution of synthetic or enamel apatite. LeGeros et al. demonstrated that the inhibition of dissolution of synthetic or enamel apatite in acid buffer was most effective in solutions containing all three ions of calcium, phosphate and fluoride (Ca+P+F), compared to that of solutions containing any combination of (Ca+P), (F+Ca) or (F+P) but the combinations of (Ca+P), (F+Ca), or (F+P) are equally effective than either Ca or P alone. (LeGeros, *J Dent Res* (1987) 66; LeGeros, J Clin Dent (1999) X: 65-73) Furthermore, the presence of F in solutions inhibit the formation of more soluble calcium phosphate phases (e.g., DCPD, octacalcium phosphate, OCP) and facilitate the formation of the less soluble F-containing apatite. (LeGeros, *Monogr Oral Sci* (1991) 15: 1-201)

Occlusion of Dentin Tubules

Gingival recession and loss of enamel or cementum layer, usually associated with aging, leads to root dentin exposure and root dentin hypersensitivity. (Cummins, *J Clin Dent* (2009) 20: 1-9) Erosive dietary foods and drinks also contribute to the loss of underlying dentin. (Zero, et al., *Int Dent J* (2005) 55: 285-290) A natural treatment to reduce dentin hypersensitivity is provided by saliva by forming a protective layer consisting of a combination of salivary glycoproteins with calcium phosphate. (Kleinberg, *Dent Today* (2002); 21: 42-47) Current effective treatment is based on occluding or blocking the exposed dentine tubules, thereby preventing the hydrodynamic mechanism is an effective treatment. (Suge, et al. *J Dent Res* (1995); 74: 1079-1085; Cummins, *J Clin Dent* (2009); 20:1-9; Pashley, *Archives of Oral Biology* (1994) 39 Suppl: 73S-80S)

Solutions containing calcium or phosphate or both have been reported to occlude dentin tubules to a lesser or greater degree. (Suge, et al. *Dent Mater J* (2005); 24: 522-529) Calcium phosphate and fluoride products have been shown to have a positive effect in occluding dentin tubules and providing relief from dentin hypersensitivity. Imai et al. showed that sequential treatment with calcium chloride solution and mono- and di-phosphate solution covered the dentin surface with calcium phosphate, but the precipitate formed only on the dentinal surface. (Imai, *Dent Mater J* (1990) 9: 167-172) Tung et al showed that amorphous calcium phosphate (ACP) was effective in covering the dentinal surface with calcium phosphate and reducing permeability but no crystals were observed within the fractured tubules. (Tung, et al. *J Endod* (1993) 19: 383-387) Addition of F⁻ ions to the post-treatment solution with the calcium phosphate precipitation formation resulted in the occlusion of dentin tubules with apatite rather than dicalcium phosphate dihydrate. (Suge, et al. *J Dent Res* (1995) 74: 1079-1085)

Fogel et al. reported dentin tubules densities for the inner root cervical dentin ranging from 32,000 to 47,000 tubules per $mm^{-2}$ and for the outer cervical dentin, ranging from 18,000 to 29,000 tubules per $mm^2$. (Fogel, et al., *J Dent Res* (1988) 67: 1381-1385) The diameter for the inner tubules varied from 1.27 to 1.85 μm and outer tubules varied from 0.9 to 1.25 μm. The mean cervical tubule density for each group of the dentin sections ranged from 28,900 to 32,499 tubules per $mm^{-2}$ and the mean tubule diameter ranged from 1.65 to 1.80 μm. The narrower range of values in our sample indicates that the dentin sections were obtained from similar areas of the root.

The present SEM images show occlusion of the dentin tubules or decrease in dentin tubule diameter after treatment with the three different solutions, with solution A3 treatment showing the highest percent of occluded dentin tubules and smallest tubule diameters. Fractured dentin sections treated with solution A2 and A3 show occlusion of the opening of the tubules and penetration into the upper part of the tubules. Fractured dentin sections treated with solution A1 show occlusion only at the opening of the tubules but did not penetrate deep into the tubules (FIG. 6).

Efficacy of CaP solutions with Zn and F Compared to Oxalate/Calcium and Oxalate/Phosphate Solutions.

The present data demonstrate that dentin surfaces treated with calcium phosphate solution containing F and Zn ions (solution A3) occlude significantly higher percent of dentinal tubules compared to dentin surfaces treated with oxalate-containing solutions (OX/Ca) or oxalate/phosphate containing solution (OX/P). In addition, the occluded precipitate from solution A3 is more resistant to acid dissolution than that from oxalate-containing solution or oxalate/phosphate-containing solution.

These data show that saturated solutions containing calcium, phosphate, fluoride and zinc ions were effective in occluding a large percentage of the dentin tubules and in providing a dentin surface that is less susceptible to acid dissolution. The efficacy of such solutions may be optimized by manipulating the solution composition and pH.

These data indicate that the calcium phosphate-based solutions are effective in occluding dentin tubules and in providing dentin surfaces and occluded dentin tubules less susceptible to acid dissolution. Such solutions may have the potential for treatment to minimize dentin sensitivity and provide a less acid-susceptible dentin surface.

These data demonstrate that the experimental saturated calcium phosphate solutions (sCaP) containing fluoride and zinc ions are effective in providing a coating on the dentin surfaces that is less susceptible to acid dissolution and that is less susceptible to *S. mutans* growth and colonization than the control. In addition, the treated surfaces showed significant number of occluded tubules and tubules with smaller diameters.

The experimental sCaP solutions used differ in pH (solution A, pH 7; solutions B, C and D, pH 5.5) and in $Zn^{2+}$ and $F^-$ ion concentrations (solution C had twice the concentration of these ions compared to solution B; solution D did not contain $Zn^{2+}$). Evidences for deposition of a coatings on surfaces include: (a) changes in surface morphology (from SEM images), (b) difference in crystallite size (from X-ray diffraction analyses), (c) difference in the organic/inorganic ratio (from FTIR analyses) of materials scraped from dentin surfaces, and (d) difference in the dissolution properties between the control and sCaP treated dentin surfaces. The material deposited was identified as an apatitic material using x-ray diffraction and FTIR analyses.

These data demonstrate that the amount of the material deposited on dentin surfaces depends on the composition and pH of the mineralizing solution. The amount deposited is greater from solutions with a lower pH and/or higher concentrations of $F^-$ and $Zn^{2+}$ ions. The lower organic/inorganic ratio calculated from the ratio of the intensities of the N—H (from the collagen) and the C—O (from the carbonate groups in the apatite) or P—O (from the phosphate groups in the apatite) indicate that the deposited calcium phosphate (apatitic) had higher mineral content.

The higher resolution of the phosphate absorption bands in the spectra of the material from the dentin surfaces treated with solutions B or C compared to that from the dentin surfaces of the control or those treated with solution A indicate a higher crystallinity in the dentin apatite from the dentin surfaces treated with solutions B or C. The higher crystallinity is due to the incorporation of fluoride ions in the apatite (LeGeros, *Monogr Oral Sci* (1991) 15(1-201); Yao, et al., *Acta Biomater* (2009) 5(6):2169-77). The higher crystallinity (i.e., larger crystal size) were also observed in greater crystallite size of dentin apatite from these surfaces as determined from their x-ray diffraction profiles.

The lower concentration of Ca ions released from surfaces treated with solutions B or C compared to that treated with solution A or control surfaces suggest that treatments with solutions B or C resulted in surfaces less susceptible to acid dissolution (i.e., less soluble). In our recent study, some surface deposits and dentin tubule occlusions (from treatment with either solutions B or C) still remained even after exposure to acidic buffer for one hour (Gu et al., in press). Incorporation of Zn ions in apatite has been shown to increase the solubility of apatite (LeGeros, *Monogr Oral Sci* (1991) 15(1-201) while incorporation in tricalcium phosphate decrease the solubility of apatite (Ito, et al., *Biomed Mater* (2006) 1(3):134-9; LeGeros, et al., *Am J. Dent* (1999) 12(2):65-71). In cases where $Zn^{2+}$ ions were simultaneously incorporated, the F effect was more dominant (LeGeros, et al., *J Fluor Chem* (1988) 41(53-64)).

Incorporation of F ions had been shown to decrease the solubility of apatite (LeGeros, *J Dent Res* 69 Spec (1990) No (567-74; discussion 634-6; LeGeros, *Monogr Oral Sci* (1991) 15(1-201); Moreno, *Int Dent J* (1993) 43(1 Suppl 1):71-80). In addition, acid exposure of the dentin surfaces treated with sCaP solutions could lead to partial dissolution of the coating releasing calcium, phosphate and fluoride ions to the microenvironment of the tooth surface which will inhibit further dissolution of the dentin surface. Solutions containing calcium (Ca), phosphate (P) and fluoride ($F^-$) ions in solution was shown most effective in inhibiting the dissolution of synthetic or enamel apatite compared to solutions containing (Ca+P), (Ca+F) or (P+F) or F ions alone, is most effective in inhibiting the dissolution of synthetic or enamel apatite by formation of fluorapatite ((LeGeros, *J Dent Res* 69 Spec (1990) No (567-74; discussion 634-6; LeGeros, *Monogr Oral Sci* (1991)).

The mechanism for the observed cariostatic effect of fluoride is a combination of (a) its inhibiting effect on the dissolution of the dental mineral; (b) enhancing mineralization; (c) formation of F- or (F, OH)-apatite crystals which are more resistant to acid dissolution (LeGeros, *Monogr Oral Sci* (1991) 15(1-201); Moreno, *Int Dent J* (1993) 43(1 Suppl 1):71-80)); (d) reducing the metabolism of oral bacteria (Van Loveren, et al., *J Dent Res* (1987) 66(11):1658-62C), and (e) formation of $CaF_2$ As early as 1940, some (Bibby, et al., *J Dent Res* (1940) 19(391-402)) reported that carbohydrate metabolism in pure cultures of oral streptococci and lactobacilli was inhibited by fluoride. Subsequent investigations concentrated on the effect of fluoride on oral bacteria and on dental plaque ecology (Bowden, et al., *Oral Microbiol Immunol* (1990) 5(6):346-51). Whether the inhibitory effect of fluoride on bacterial growth and colonization contribute to its cariostatic property is still been debated (Tatevossian, *J Dent Res* (1990) 69 Spec No (645-52; discussion 682-3). Dental plaque colonization is one of the very important parameters for determining the effect of fluoride on oral bacteria (Hamilton, *J Dent Res*, (1990) 69 Spec No (660-7; discussion 682-3). In vitro experiments have shown that approximately 9,500 ppm F- in solution is needed to inhibit adsorption of bacteria on hydroxyapatite (Rolla, et al., *Caries Res* (1975), 9(1):66-73). This means that the $F^-$ ion concentrations needed to provide antimicrobial effects significantly exceed the concentration needed to reduce the solubility of apatite (Tatevossian, *J Dent Res* (1990) 69 Spec No (645-52; discussion 682-3).

In a biofilm model, Li et al., *J Dent Res* (1994) 73(10): 1615-26 showed no difference in the initial growth (initial 20 hours) of mutants streptococci between F-free and F-substituted apatite. Their study showed that only at low environmental pH (pH 5.5) or under glucose excess, was the accumulation of *S. mutans* cells on the F- apatite surfaces significantly reduced.

These results showed that dentin sections treated with solution D which had the same F ion concentration but did not contain $Zn^{2+}$ ions as solution C, had no significant antibacterial property. Solutions B and C which had both $F^-$ and $Zn^{2+}$ ions can cause the formation of thin coating of apatite containing $F^-$ and $Zn^{2+}$ on the dentin surfaces. Such coating inhibited bacterial attachment and colonization compared to control or to dentin surfaces treated with solution D. This suggests that $Zn^{2+}$ was more effective than the $F^-$ (at least at the low concentrations used) in inhibiting adherence and colonization of *S. mutans* to dentin surfaces. $Zn^{2+}$ and $F^-$ ions may act synergistically in inhibiting bacterial colonization. Further studies are needed to clarify this issue.

Meurman, *Caries Res* (1988) 22(5):283-7 reported that treatment of *S. mutans* with F did not significantly affect its ultrastructure and its adsorption to hydroxyapatite, but treatment with chlorhexidine gluconate alone or in a combination with F significantly reduced *S. mutans* growth and adsorption. Shani et al. *Caries Res* (2000) 34(3):260-7 also reported that preincubation of saliva-coated hydroxyapatite beads with an amine fluoride solution significantly reduced the number of viable cells in forming significantly reduced the number of viable cells in forming an *S. sobrinus* biofilm whereas preincubation with NaF or chlorhexidine alone did not. In humans, plaque deposition was reduced after the use of rinses and toothpaste with stannous fluoride (Tinanoff, et al., *Pediatr Dent* (1979) 1(3):199-204). White et al. (White, et al., *J Clin Dent* (1995) 6 Spec No (84-8) reported that experiments with the so-called plaque glycolysis and regrowth method demonstrated a reduced acidogenicity of dental plaque 45 min after the use of $SnF_2$ dentifrice. Therefore, although there is sufficient evidence that fluoride has antibacterial activity, this activity is present only when the fluoride is associated with $Sn^{2+}$ or with amine (Shani, et al., *Caries Res* (2000) 34(3): 260-7).

Zinc salts have been included in several dental products because of their antibacterial properties (Giertsen, et al., *J Dent Res* (1989b) 68(6):1132-4). Zinc coating on titanium alloy, orthodontic brackets coated with Zn-containing amorphous calcium phosphate (Zn-ACP) and polymeric membranes mineralized with Zn—CaP were shown to inhibit bacterial growth and colonization (Alsilmi, et al., *J Dent Res* (2003) (2112); Chou, et al., *Implant Dent* (2007) 16(1):89-100 Park, et al., *J Dent Res* (2005) 84 (1917)).

Treatment with $F^-$ and $Zn^{2+}$ containing saturated calcium phosphate solutions resulted in the formation of $F^-$ and $Zn^{2+}$ containing apatite on dentin surfaces. The present data demonstrates that dentin surfaces treated with solutions containing $Zn^{2+}$ ions in addition to the $Ca^{2+}$, $HPO_4^-$ and $F^-$ ions (solutions B and C) inhibit bacterial attachment and colonization. Although solution C had double the $Zn^{2+}$ ion concentration of solution B, dentin sections treated with solution C show no higher antibacterial effect compared to solution B.

Giertsen et al. (Giertsen, et al., *Caries Res* (1989a) 23(4):272-7) found a dose-related effect of $ZnCl_2$ on dental plaque formation. They showed that 100 mM $Zn^{2+}$ compared 5 mM $Zn^{2+}$ in solution was significantly more effective in inhibiting plaque formation.

Treatment of dentin surfaces with saturated calcium phosphate solutions containing F and $Zn^{2+}$ ions resulted in a significant number of occluded dentin tubules and in a decrease in dentin diameters. (Gu, et al., *Am J. Dent* (2011) (in press)). Since dentin hypersensitivity has been associated with exposed open dentin tubules and large dentin tubule diameters (Ishikawa, et al., *J Dent Res* (1994) 73(6):1197-204; Suge, et al., *Dent Mater J* (2005) 24(4):522-9), these data suggest that such solutions may be used for treating dentin hypersensitivity.

These results show that treating acidic saturated calcium phosphate solutions containing $F^-$ and $Zn^{2+}$ ions causes formation of a thin coating of apatite incorporating and $Zn^{2+}$ ions which minimizes acid dissolution of dentin surfaces and inhibits bacterial attachment, growth and colonization. The calcium phosphate-based solutions containing both fluoride and Zn ions may have mineralizing, acid resistance and antibacterial effects and may be potentially useful as a strategy against dentin caries formation and progression.

Oral Compositions

Those of skill in the art will appreciate that the dosage of the present compositions administered will vary due to a number of factors, such as, for example, the age of the patient and severity of oral disease or tooth decay, whether the treatment is therapeutic or prophylactic in nature, the pharmacodynamic characteristics of the particular agent, the duration of the topical application, the age, health, and weight of the patient; the nature and extent of symptoms, the kind of concurrent treatment, and the effect desired. As a general rule, the solution or suspension will be held in the mouth for at least one minute, with vigorous agitation to rinse as much of the surfaces of the oral cavity as possible. After rinsing, the solution or suspension may be expectorated, or may be swallowed in some instances. Deviations from these ranges that produce the therapeutic effects without significant harm to the patient are considered to be within the scope of the present claims. The present methods maximize contact with the dental surfaces of the patient.

The compositions of the present invention such as oral rinses or mouthwashes may be used either alone or in combination with other ingredients or treatments. By "in combination with," is meant that the components are administered at the same time or sequentially in any order at different points in time. When administered at different points in time, the components should be administered sufficiently closely in time to produce the desired therapeutic effect.

Compositions of the present invention include low-alcohol oral care compositions.

For dentifrice compositions suitable abrasives include precipitated silica or silica gels which have an average particle size ranging from about 0.1 to about 50 microns. Preferred silica abrasives include those marketed under the tradename "Sylodent™" or "Syloid™" by W.R. Grace & Co. and "Zeodent™" marketed by J. M. Huber Corp. Other suitable abrasives, having a suitable particle size as described above, include β-phase calcium pyrophosphate, alumina and calcium carbonate. The amount of abrasive in a dentifrice composition ranges up to about 60% by weight, preferably from 10% by weight to 40% by weight.

Dentifrice and oral rinse compositions also may contain a suitable fluoride source. Typical sources include soluble salts of the fluoride ions, e.g. sodium fluoride, potassium fluoride, stannous fluoride, stannous fluorozirconate etc., or soluble salts of monofluorophosphate, e.g. sodium monofluorophosphate, etc. One preferred fluoride source is sodium fluoride. The fluoride ion source may be sufficient to provide from about 50 ppm to about 2,500 ppm fluoride, preferably from about 250 ppm to about 1500 ppm for dentifrices and from about 50 ppm to about 250 ppm fluoride for oral rinses.

A liquid carrier generally includes mixtures of water and ethanol for oral rinses, although the carrier can be alcohol-free, especially in dentifrices. For oral rinses, the amount of water ranges upwards from about 25% by weight. The amount of alcohol ranges by weight from about 0% to about 25% by weight, preferably from about 0% by weight to about 15% by weight. For dentifrices, the amount of water ranges from about 0% by weight to about 60% by weight, preferably from about 0% by weight to about 40% by weight.

The pH of the oral rinses and dentifrice compositions may range from about 3.5 to about 8.5, or from about 4.0 to 8.0, or from about 4.5 to 7.5, or 5.0 to 7.0.

The oral rinse compositions are unusually stable so as to be substantially clear and substantially free of precipitation, flocculation, or crystal formation at about room temperature (about 25° C.) as well as at low temperatures of at least about 5° C. for at least about 1 week. The low temperature stability of these compositions is determined by cooling the compositions to about 5° C., storing for at least seven days and determining whether any precipitate, crystallized or flocculated material is formed in the clear compositions (solutions and gels).

Oral surfactants useful in the present invention include nonionic and anionic surfactants. Oral surfactants employed include block co-polymers of polyoxyethylene and polyoxypropylene such as the Pluronics from BASF. Other oral surfactants include soluble alkyl sulfonates having 10 to 18 carbon atoms, such as sodium lauryl sulfate, and sulfates of monoglycerides of fatty acids having 10 to 18 carbon atoms or sarcosinates (including salts and derivatives) such as sodium-N-lauroyl sarcosinate. Mixtures of anionic and nonionic surfactants can be used. These ingredients are generally present from about 0% by weight to about 4% by weight, preferably from about 0% by weight to about 1% by weight for oral rinses and from, about 0.5% by weight to about 4% by weight for dentifrices.

Additional antiplaque agents can also be optionally added to the compositions. These include cetyl pyridinium chloride and related quaternary salts, chlorhexidine, zinc salts such as zinc chloride, stannous salts such as stannous chloride or stannous fluoride and peroxygens such as hydrogen peroxide and carbamide peroxide. These optional antiplaque agents are generally present at levels ranging form about 0% to about 5% by weight.

Additional anticalculus agents can be optionally added to the compositions. These include tetra-alkali or di-alkali metal pyrophosphate salts and zinc salts, such as, but not limited to, zinc chloride etc. These optional anticalculus agents are generally present at levels ranging from about 0% by weight to about 10% by weight for pyrophosphate salts and from about 0% by weight to about 3% by weight for zinc salts.

In the compositions of the invention, preservatives may be used, especially for non-alcohol or low alcohol compositions. These include benzoic acid, sodium benzoate, methylparaben, propylparaben, sorbic acid and potassium sorbate. These optional preservative agents are generally present at levels ranging from about 0% by weight to about 2% by weight.

In the compositions of the invention, buffering systems may be used to stabilize the pH in the product. Typical buffering systems include, but are not limited to, citrate, benzoate, gluconate and phosphate. Buffering systems are present in concentrations from about 0.01% by weight to about 1% by weight.

In addition to the above ingredients, the invention may include other optional ingredients to impart desired mouth feel and provide flavoring and coloring. Humectants are an optional component of the compositions. For oral rinses they impart a moist and elegant feel to the mouth and in toothpaste compositions they prevent hardening on exposure to air. Some humectants can provide sweetness to the composition. Suitable humectants include edible polyhydric alcohols such as glycerin, sorbitol, propylene glycol and xylitol. The humectant generally is present in an amount ranging from 0% by weight to 30% by weight for oral rinses and 0% by weight to 70% by weight for dentifrice compositions.

Thickening agents or binders are an optional component of the compositions. Typical thickening include, xanthan gum, carrageenan, carboxyvinyl polymers, carbomers, cellulose gums such as carboxymethyl cellulose, cellulose derivatives such as hydroxyethylcellulose and silicas. Thickeners may be present in the compositions from about 0% by weight to 2% by weight. Xanthan gum is the preferred thickener in oral rinses. In dentifrices, silica-based thickeners can be used at concentrations from 0% by weight to about 20% by weight, e.g. "Sylox™".

Flavoring agents may also be added to the compositions. The flavorant may be a flavoring oil or mixture of flavoring oils such as oil of peppermint, spearmint, wintergreen, clove, sassafras, lemon, orange or lime. Sweetening agents such as saccharin, lactose, maltose, aspartame, sodium cyclamate, polydextrose etc. may be added to the compositions. Flavoring agents generally are present in an amount ranging from 0.001% by weight to about 0.5% by weight for oral rinses and 0.25% by weight to about 5% by weight for dentifrice compositions. Sweetening agents generally are present in an amount ranging from 0.001% by weight to about 5% by weight for oral rinse and dentifrice compositions. Coloring agents generally are present in an amount ranging from 0% by weight to 0.01% by weight.

EXAMPLE 1

Materials and Methods

Preparation of the Calcium Phosphate Solutions (CaPs)

Supersaturated mineralizing solutions were prepared from mixtures of calcium deficient apatite (prepared by precipitation), sodium fluoride and zinc chloride (Fisher Scientific, New Jersey). The experimental solutions (A1, A2 and A3) were supersaturated with respect to F- and Zn-substituted apatite. A1 and A2 have similar composition but different pH values: pH 7.0 for A1 and pH 5.5 for A2. Solutions A2 and A3 had the same pH (5.5) but the A3 solution had twice the concentrations of $F^-$ and $Zn^{2+}$ ions compared to A2. The actual compositions of solutions A1, A2 and A3 are provided as follows:

Solution A: 1 g Calcium deficient apatite (CDA)+20 mg NaF+10 mg $ZnCl_2$ in 10 ml 4.25% $H_3PO_4$, pH adjusted to 7 with NaOH Solution A2: 1 g Calcium deficient apatite (CDA)+20 mg NaF+10 mg $ZnCl_2$ in 10 ml 4.25% $H_3PO_4$, pH adjusted to 5.5 with NaOH Solution A3: 1 g Calcium deficient apatite (CDA)+40 mg NaF+20 mg $ZnCl_2$ in 10 ml 4.25% $H_3PO_4$, pH adjusted to 5.5 with NaOH Oxalate (OX/Ca) solution contained 1.6M $K_2C_2O_4$ and 1.1M $CaCl_2$. OX/P solution contained 1.6M $K_2C_2O_4$ and 1.7M $KH_2PO_4$. The oxalate concentration in OX/Ca, OX/P is similar to that used in the commercially available oxalate product for DH. All solutions were adjusted to pH 5.5.

Preparation of the Dentin Sections

Dentin samples were obtained from extracted unerupted third molars from human adults (18-25 years old) collected from the Department of Maxillofacial Surgery, New York University College of Dentistry, stored in saline and sterilized using gamma radiation. The crowns were removed using a water-cooled diamond-bladed saw (Series 15 HC Diamond, N 11-4244, Buehler, USA) and the roots were attached to mounting stubs with epoxy resin. Root sections were prepared by using a low-speed diamond saw. Cuts were made parallel to the long axis of the root and the roots divided mesio-distal direction to obtain buccal 1/2nd or lingual 1/2nd dentin sections (FIG. 1). The dentin slices were then polished on one side using 320 grit, 600 grit, then 1000 grit wet paper and a polishing wheel to create an even and uniform surface. The specimens were further polished by using a polishing cloth (Buehler, USA), which was made wet with 1 micron monocrystalline diamond suspension (Buehler, USA). Each section was polished for approximately 30 seconds to make each specimen shiny. The dentin slices were then examined under a microscope to confirm that the surface was uniformly polished. The polished specimens were then placed in a glass bottle of doubly distilled water (DDW) and cleaned with ultrasonic cleaner to remove the polishing abrasive material. After ultrasonic cleaning, the specimens were rinsed with DDW and dried with compressed air.

Treatment of the Dentin Sections

The dentin sections were treated as follows: Group A—control (treated with double distilled $H_2O$, DDW) and Groups A1, A2 and A3 treated with solutions A1, A2 and A3, respectively, for a period of 4 minutes rinsed in DDW and dried with compressed air and stored in a dessicator until needed for analysis. Three groups of dentin sections Group A3, Group OX/Ca and Group OX/P were treated with solution A3, OX/Ca and OX/P respectively.

Measurement of the Dentin Tubule Density

To measure the dentinal tubule densities, six dentin sections for each group were prepared as described above. Cervical areas on the dentin surfaces were photographed at 6 k magnifications. Tubules were counted on 6 root dentin sections for each group. Three SEM fields per root dentin sections and approximately 100 tubules per field were counted. Mean tubule densities were expressed in number of tubules per square mm.

Characterization of the Treated and Control Dentin Surfaces

Characterization of Dentin Surface Morphology.

The treated and control dentin sections were mounted on aluminum stubs with graphite adhesive and sputter coated with gold and characterized using scanning electron microscopy, SEM (JEOL JSM-5400; JEOL USA, Inc., Peabody, Mass.; and Hitachi S-3500N; Hitachi, Ltd., Tokyo, Japan). Images were taken from selected fields in the cervical portion of each section at varying magnifications (×2 k, ×10 k and ×20 k). Several untreated and dentin sections treated with solution A1, A2 and A3 were further fractured to reveal crystals within the dentin tubules and examined by SEM.

Measurement of the Dentin Tubule Diameter

To measure the tubule diameters of the control and treated groups, six dentin sections selected from each of the groups were mounted on aluminum stubs with graphite adhesive and sputter coated with gold and characterized using scanning electron microscopy, SEM (JEOL JSM-5400; JEOL USA, Inc., Peabody, Mass.; and Hitachi S-3500N; Hitachi, Ltd., Tokyo, Japan). Cervical areas on the dentin surfaces were photographed at 5000×. Tubule diameters were measured on SEM prints to the nearest 0.01 mm, by means of an electronic digital caliper. Mean tubule diameters were expressed in μm. A total of 90 inner tubules were measured for each group.

Determination of Percent Occlusion of the Dentin Tubules (DT)

To determine the percent of occluded dentinal tubules, SEM images of the same magnification (×2 k) were used. The ratio of the number of occluded dentin tubules (ODT) to the total number of dentin tubules (TDT) per defined random areas per section was determined. Per cent (%) occlusion was calculated as (ODT/TDT)×100. Six equivalent areas for each of three dentin sections for each group were measured and the mean±SD was calculated.

Dissolution Experiments

The extent of dissolution of the control and treated dentin surfaces was determined by monitoring the release of calcium ions in an acidic buffer (0.1M KAc, pH 6, 37° C.) with time using inductive coupled plasma (Thermo Jarrell Ash Model-Trace Scan Inductive Coupled Plasma, Waltham, Mass.). These experiments were carried out as follows: nail varnish was applied on all parts of the root dentin sections except for a circular area (diameter, 5 mm) on each of the treated or control surfaces, each dentin section was immersed in acidic buffer (0.1M KAc, pH 6, 37° C.), and the release of calcium ($Ca^{2+}$) ions into the buffer with time was monitored.

Changes in surface morphology after exposure to the acid buffer of the treated surfaces compared to the control surfaces were observed using SEM.

Statistical Analysis

All results were expressed as mean±SD ($\bar{x}$±s) of the measurements. Statistical analysis was assessed by using one-way ANOVA followed by Student-Newman-Keuls or Dunnett's T3 post hoc test, for individual between-group comparisons. α=0.05.

Results

Morphology of Treated and Untreated Dentin Surfaces

The mean cervical tubule density for the control group ranged from 28,900 to 32,499 tubules per $mm^{-2}$ and the mean tubule diameter ranged from 1.65 to 1.80 μm.

Figure 2A:
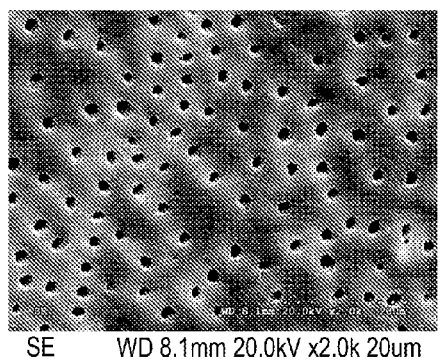
FIG. 2 provides SEM images showing crystal deposits on treated dentin surfaces but not on the control surfaces (FIG. 2B compared with FIGS. 2D, 2F and 2H). The amount of the crystals deposited on the surfaces appeared to depend on the composition and pH of the mineralizing solution. For surfaces that were treated with solutions (A2 and A3) with the similar pH (5.5), greater amount of crystal deposits were observed on surfaces treated with solution with higher F and Zn ion concentrations (solution A3 vs solution A2) as shown in FIG. 2H vs FIG. 2F. For surfaces treated with solutions of the same F and Zn ion concentration but with different pHs, greater amount of crystal deposits were observed on surfaces treated with solutions with lower pH 5.5 (A2) compared to that with solution with higher pH 7 (A1) as shown in FIG. 2D compared to FIGS. 2F and 2D.
Figure 2B:
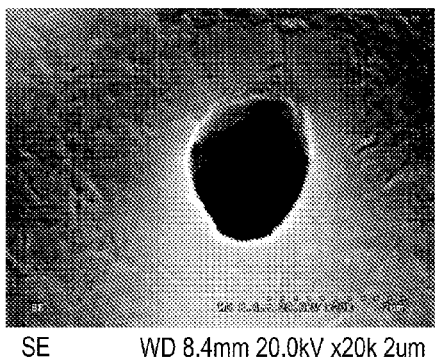
Figure 2C:
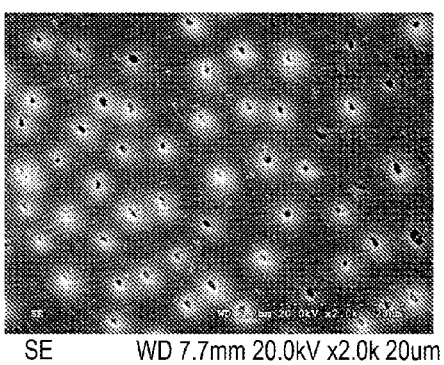
Figure 2D:
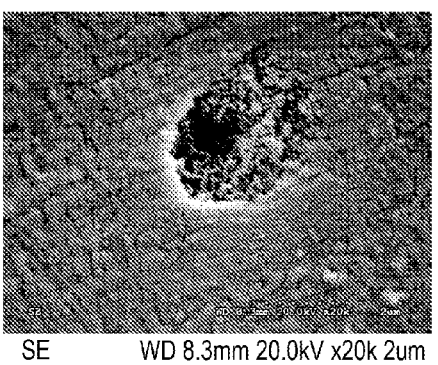
Figure 2E:
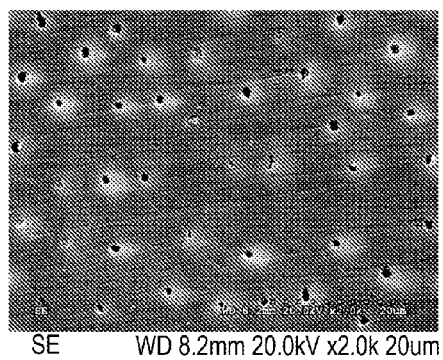
Figure 2F:
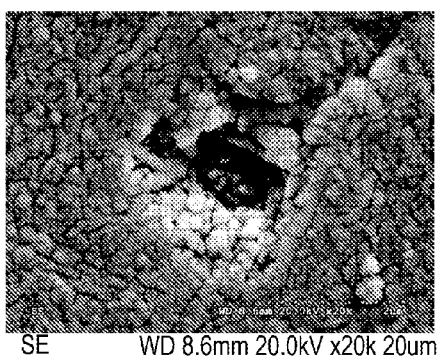
Figure 2G:
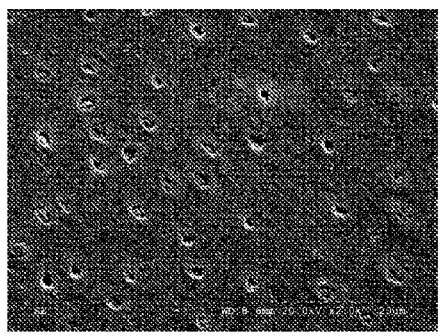
Figure 2H:
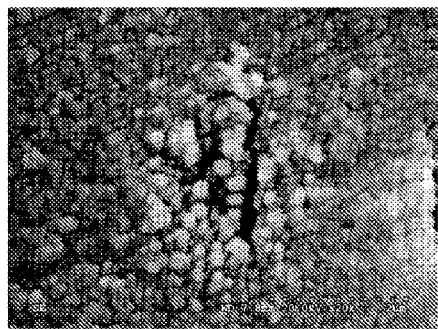

SEM images showed crystal deposits on the treated dentin surfaces but not on the control surfaces (FIG. 2B compared with FIGS. 2D, 2F and 2H). The amount of the crystals deposited on the surfaces depended on the composition and pH of the mineralizing solution. For surfaces that were treated with solutions (A2 and A3) with the similar pH (5.5), greater amounts of crystal deposits were observed on surfaces treated with solution with higher F and Zn ion concentrations (solution A3 vs solution A2) as shown in FIG. 2H vs FIG. 2F. For surfaces treated with solutions of the same F and Zn ion concentration but with different pHs, greater amounts of crystal deposits were observed on surfaces treated with solutions with lower pH 5.5 (A2) compared to that with solution with higher pH 7 (A1) as shown in FIG. 2D compared to FIGS. 2F and 2D.

Tubule Diameter of Control and Treated Dentin

Figure 3A:
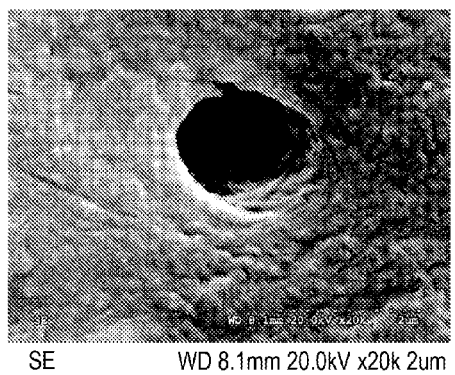
FIG. 3 provides SEM images showing that in the same section of treated dentin, most of the tubules were totally occluded (FIGS. 2C-1H), while in other areas, the diameter of the dentin tubules decreased (FIGS. 3B, 3C and 3D compared to FIG. 3A).
Figure 3B:
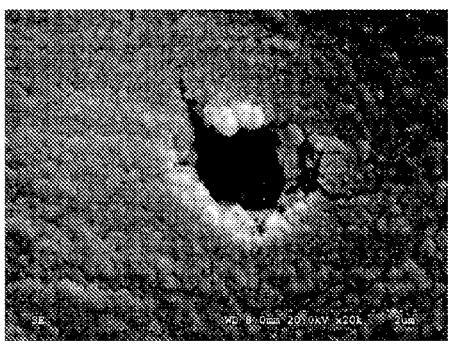
Figure 3C:
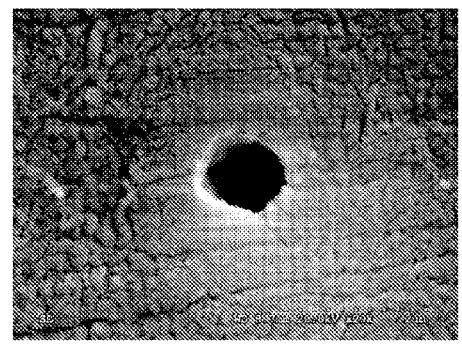
Figure 3D:
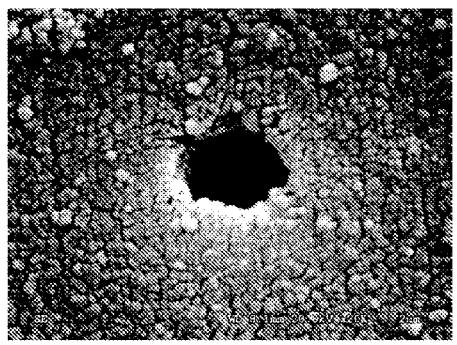

SEM images show that in the same section of treated dentin, most of the tubules were totally occluded (FIGS. 2C-1H), while in other areas, the diameter of the dentin tubules decreased (FIGS. 3B, 3C and 3D compared to FIG. 3A). Dentin surfaces treated with solution A2 and A3 at pH 5.5 (FIGS. 2E and 2G) showed a higher number of occluded dentin tubules compared to the control (FIG. 2A) or those treated with solution A1 at pH 7.0 (FIG. 2C).

Figure 4:
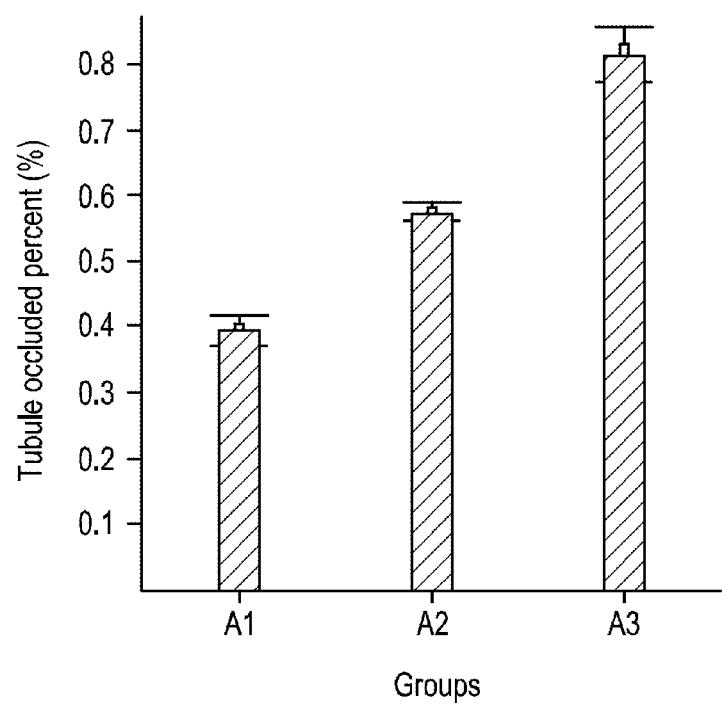
FIG. 4 provides the percent of tubules occluded from each group after dentin sections from human molars were prepared and divided into groups: Group A—control (treated with double distilled $H_2O$), Groups A1, A2 and A3 were treated with experimental solutions supersaturated with respect to F- and Zn-substituted calcium phosphates. Solutions A1 and A2 were similar in composition but differed in pH values (A1, pH 7.0; A2, pH 5.5). Solutions A2 and A3 were similar in pH (pH 5.5) but the A3 solution had twice the concentrations of $F^-$ and $Zn^{2+}$ ions compared to A2. Another group of dentin sections were treated A3 solution, oxalate solution containing Ca (OX/Ca) and OX solution containing P(OX/P). The control and treated dentin sections were characterized using scanning electron microscopy.
Figure 5:
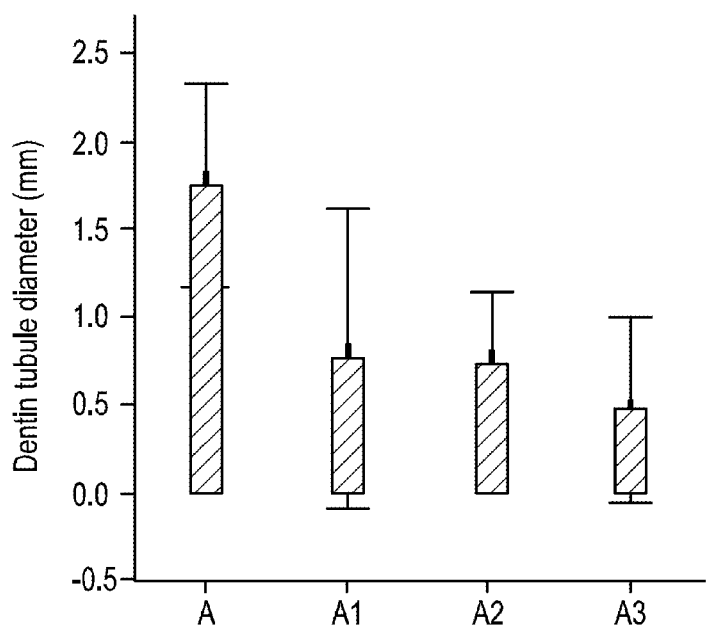
FIG. 5 provides the mean dentin tublule diameter of each group after dentin sections from human molars were prepared and divided into groups: Group A—control (treated with double distilled $H_2O$), Groups A1, A2 and A3 were treated with experimental solutions supersaturated with respect to F- and Zn-substituted calcium phosphates. Solutions A1 and A2 were similar in composition but differed in pH values (A1, pH 7.0; A2, pH 5.5). Solutions A2 and A3 were similar in pH (pH 5.5) but the A3 solution had twice the concentrations of $F^-$ and $Zn^{2+}$ ions compared to A2. Another group of dentin sections were treated A3 solution, oxalate solution containing Ca (OX/Ca) and OX solution containing P(OX/P). The control and treated dentin sections were characterized using scanning electron microscopy.
Figure 6A:
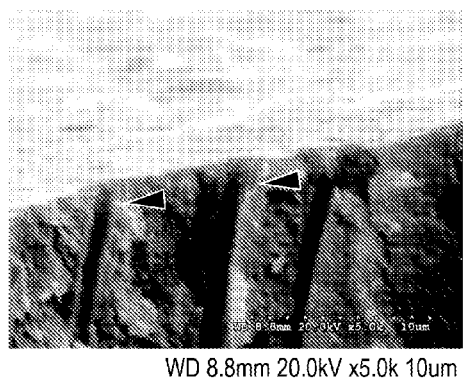
FIG. 6 demonstrates that fractured specimens showed penetration of the crystals in dentin sections treated with solutions A2 and A3 (FIGS. 6C and 6D).
Figure 6B:
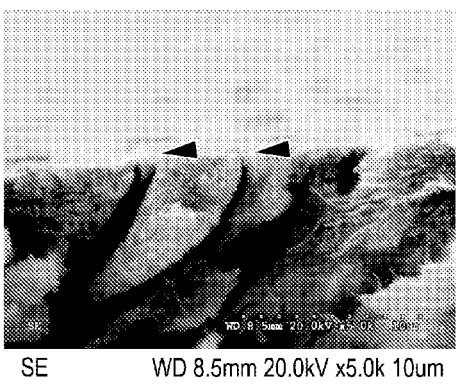
Figure 6C:
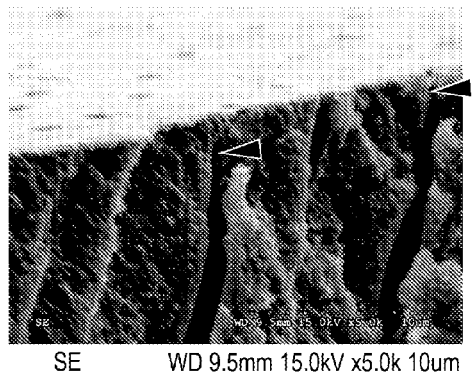
Figure 6D:
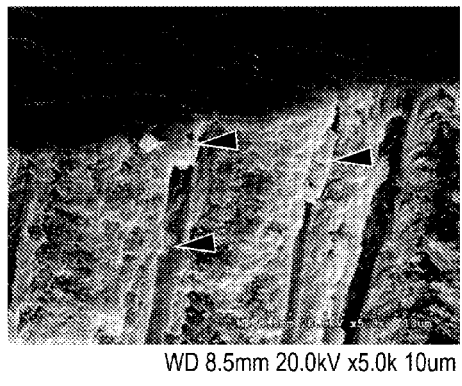

The percent of occluded dentin tubules ranged from 38% to 40% for surfaces treated with solution A1; 57% to 58% for surfaces treated with solution A2; and 80% to 83% for surfaces treated with solution A3 (FIG. 4). There was a significant difference of the percentage of tubule occlusion between A1 and A2, between A2 and A3, and between A1 and A3. The mean cervical tubule diameter for group A was 1.75±0.23 μm (Mean±SD), for dentin tubules treated with solutions A1, A2 and A3 were 0.76±0.35 μm, 0.72±0.17 μm and 0.48±0.22 μm respectively (FIG. 5). There was a significant difference between each treated group and control group A, between group A1 and A3, and between A2 and A3. There was no significant difference between each two treated group. Fractured specimens showed penetration of the crystals in dentin sections treated with solutions A2 and A3 (FIGS. 6C and 6D).

Morphology after Exposure to Acidic Buffer

A change was observed in the morphology of the dentin surfaces after exposure to the acidic buffer for one hour. SEM images of dentin surfaces after exposure to acidic buffer for one hour showed an increase in the dentin tubule diameters (FIG. 7). However, the diameters of the dentin tubules of the treated dentin were still smaller compared to those of the control (FIG. 7D, 7F, 7H compared to FIG. 7B) similar to the difference observed before exposure to acid (FIG. 7C, 7E, 7G compared to FIG. 7A). In addition, erosion of the walls of the dentin tubules of the control dentin (FIG. 7B) was observed but not of the treated dentin after exposure to the acidic buffer (FIG. 7D, 7F, 7H). Some deposits remained on the dentin surfaces treated with solutions A2 (FIG. 7F compared with 7E) or A3 (FIG. 7H compared with 7G) even after exposure to the acidic buffer.

Comparison of Dentin Sections Treated with Solutions A3, OX/Ca and OX/P (a) Dentinal Tubule Occlusion.

The percent of occluded dentinal tubules was 86% for surfaces treated with solution A3; 54% for surfaces treated with solution OX/Ca and 50% for surfaces treated with solution OX/P. After dentin sections were immersed in 25 ml acidic buffer (0.1M KAc, pH 6, 37° C.) for 30 minutes, the percent of remaining occluded dentinal tubules was 67% for surfaces treated with solution A3; 11% for surfaces treated with solution OX/Ca and 20% for surfaces treated with solution OX/P. (Table 1) The number of occluded dentinal tubules after treatment with OX/Ca and OX/P solutions were significant decreased (P<0.01) after 30-minute exposure to the acid buffer compared to the decrease in the number of occluded dentinal tubules after treatment with solution A3. Significant differences (P<0.01) in the number of occluded dentinal tubules between groups treated with A3 solution and group treated with OX/Ca solution; and between groups treated with A3 solution and group treated with OX/P solution before and after 30-minute exposure to the acid buffer. There was no significant difference (P>0.05) between groups treated with OX/Ca solution and the group treated with OX/P solution. Group treated with solution A3 gave the highest number of occluded dentinal tubules before and after 30-minute exposure to the acid buffer. Dentin surfaces treated with solutions OX/Ca and OX/P showed considerably lower number of occluded dentinal tubules before and after exposure to the acidic buffer.

TABLE 1

The percent of dentin tubule occlusion before and after exposure to the acidic buffer ($\bar{x} \pm s$)

|  | Before acid exposure | After acid exposure |
|---|---|---|
| A3 | 85.7 ± 7.6 | 67.0 ± 9.2** |
| OX/Ca | 53.8 ± 11.3## | 11.3 ± 6.0##** |
| OX/P | 50.3 ± 8.4## | 20.5 ± 9.0##X-X-** |

Compare with % dentin tubule occlusion before exposure to the acidic buffer,
**P < 0.01; compare with A3 group,
## P < 0.01; compare with OX/Ca group, P < 0.01.
Acidic buffer: 0.1M KAc, pH 6.0, 37° C.

(b) Stability of Precipitates in Dentinal Tubules after Exposure to Acid Buffer.

Figure 8A:
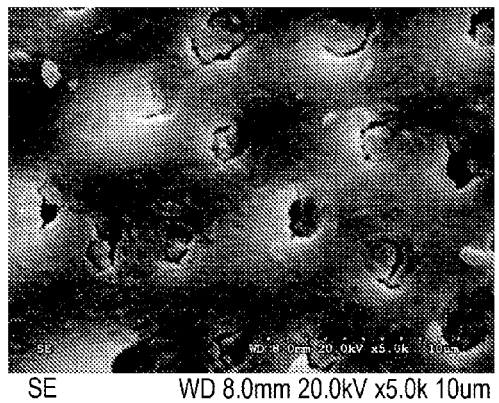
FIG. 8 demonstrates that changes were observed in the morphology of the dentin surfaces after exposure to the acidic buffer for 30 minutes (FIG. 8). Most of the occluded precipitate in the dentinal tubules after treatment with solution A3 still remained inside the tubules (FIG. 8A) while those in the dentinal tubules after treatment with solutions OX/Ca and OX/P was dissolved after 30 minute exposure to acidic buffer (FIG. 8B and FIG. 8C).
Figure 8B:
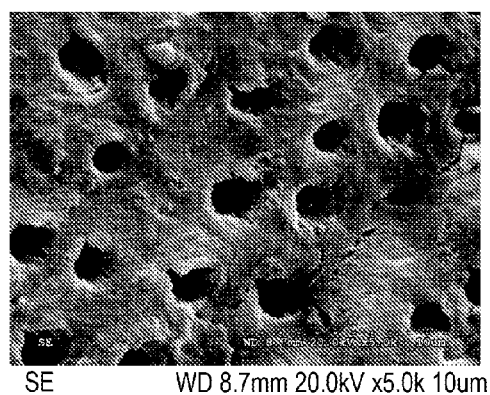
Figure 8C:
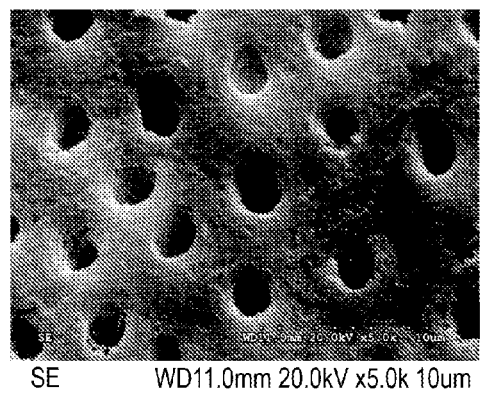

Changes were observed in the morphology of the dentin surfaces after exposure to the acidic buffer for 30 minutes (FIG. 8). Most of the occluded precipitate in the dentinal tubules after treatment with solution A3 still remained inside the tubules (FIG. 8A) while those in the dentinal tubules after treatment with solutions OX/Ca and OX/P was dissolved after 30 minute exposure to acidic buffer (FIG. 8B and FIG. 8C).

EXAMPLE 2

Materials and Methods

Preparation of the Calcium Phosphate Solutions

Double distilled water (DDW) was the control solution. The experimental saturated calcium phosphate (sCaP) solutions were prepared from mixtures of calcium deficient apatite (prepared by precipitation), sodium fluoride with or without zinc chloride (Fisher Scientific, New Jersey). The experimental solutions (A, B and C) were supersaturated with respect to F- and Zn-substituted calcium phosphates. Solutions A and B were similar in composition but differed in pH: A, pH 7.0; B, pH 5.5). Solutions B, C and D had the same pH (5.5) but solution C had twice the concentrations of $F^-$ and $Zn^{2+}$ ions compared to solution B and Solution D had the same F ion concentration as solution C but without $Zn^{2+}$ ions. The actual compositions of the solutions are provided as follows:

Solution A: 1 g Calcium deficient apatite (CDA)+20 mg NaF+10 mg $ZnCl_2$ in 10 ml 4.25% $H_3PO_4$, pH adjusted to 7 with NaOH Solution B: 1 g Calcium deficient apatite (CDA)+20 mg NaF+10 mg $ZnCl_2$ in 10 ml 4.25% $H_3PO_4$, pH adjusted to 5.5 with NaOH Solution C: 1 g Calcium deficient apatite (CDA)+40 mg NaF+20 mg $ZnCl_2$ in 10 ml 4.25% $H_3PO_4$, pH adjusted to 5.5 with NaOH Solution D: 1 g Calcium deficient apatite (CDA)+40 mg NaF in 10 ml 4.25% $H_3PO_4$, pH adjusted to 5.5 with NaOH Preparation of Tooth Specimens Human teeth specimens were obtained from extracted permanent human molars collected from the Department of Maxillofacial Surgery of the New York University College of Dentistry, stored in saline and sterilized by gamma radiation. The crowns were removed using a water-cooled diamond-bladed saw (Series 15 HC Diamond, N 11-4244, Buehler, USA) and the roots were attached to mounting stubs with epoxy resin. Root sections were prepared by use of a low-speed diamond saw. Cuts were made parallel to the long axis of the root and the roots divided mesio-distal direction to obtain buccal 1/2nd or lingual 1/2nd dentin sections (Gu et al., in press). The dentin sections were then polished on one side using 320 grit, 600 grit, then 1000 grit wet paper and a polishing wheel to create an even and uniform surface. The polished specimens were then placed in a glass bottle containing DDW, and cleaned with ultrasonic cleaner to remove the polishing abrasive material. After ultrasonic cleaning, the specimens were rinsed with DDW and dried with compressed air.

The dentin sections were randomly distributed into control group and treated groups (Groups A, B and C) reflecting the treatment solutions used. 6 sections for each group A, B or C, Groups A, B and C were immersed in sCaP solutions for a period of 4 minutes rinsed with DDW and dried with compressed air, control group was immersed in DDW for the same amount of time.

Characterization of Control and Treated Dentin Surfaces.
(a) Characterization of Surface Morphology.

The treated and control dentin sections were mounted on aluminum stubs with graphite adhesive and sputter coated with gold and characterized using scanning electron microscopy, SEM (JEOL JSM-5400; JEOL USA, Inc., Peabody, Mass.; and Hitachi S-3500N; Hitachi, Ltd., Tokyo, Japan). Images were taken from selected fields in the cervical portion of each section at varying magnifications (×2 k, ×10 k and ×20 k).

(b) Characterization of Dentin Surface Composition Using X-Ray Diffraction and FT-IR Spectroscopy.

The dentin surfaces were characterized using x-ray diffraction, XRD (Philips X' Pert X-ray diffractometer), with a curved crystal monochromator and Cu $K_\alpha$ radiation, operating at 45 kV and 45 mA, scanning in 2θ range of 25 to 35°2θ, at a rate of 0.02°2θ/10 s/step. Crystallite sizes were determined from the broadening at half height width (β1/2) of the [002] diffraction peaks using the Debye-Scherrer formula: $t=0.9\lambda/\beta_{1/2} \cos \theta$, where t=crystallite size, $\beta_{1/2}$=the difference between sample and instrumental broadening. (Klug and Alexander, 1974) Synthetic F-apatite powder was used to determine instrumental broadening.

A Fourier transform infrared spectroscopy, FT-IR (NicoletMagna IR 550 Spectrometer Series II, France) was used to determine the spectral properties of the treated and control dentin surfaces. Pellets were prepared by mixing 1 mg of the powdered material scraped from the dentin surfaces with 250 mg of KBr (IR grade) and pressing at 10,000 psi using a hydraulic press (Carver laboratory press, mode C, Ser. No. 3300-577, Fred S. Carver Inc.). Each spectrum covered the range from 4000 to 400 $cm^{-1}$. The assignment of absorption bands were according to spectroscopic studies on carbonate apatites and other calcium phosphates (LeGeros, et al., *Dev Appl Spectrosc* (1970) 7B:3-12; LeGeros, *Monogr Oral Sci* (1991) 15(1-201).

Dissolution Experiments

The extent of dissolution of the control and treated dentin surfaces was determined by monitoring the release of calcium ions in an acidic buffer (0.1M KAc, pH 6, 37° C.) with time using inductive coupled plasma (Thermo Jarrell Ash Model-Trace Scan Inductive Coupled Plasma, Waltham, Mass.). These experiments were carried out as follows: nail varnish was applied on all parts of the dentin surfaces except for a circular area (diameter, 5 mm) on each of the treated or control surfaces; each dentin section was immersed in acidic buffer (0.1M KAc, pH 6, 37° C.); and the release of calcium ($Ca^{2+}$) ions into the buffer with time was monitored.

Preparation of Bacteria

A reference strain of *S. mutans* ATCC 25175 was used for the in vitro adherence tests. The bacteria was suspended in 200 ml brain heart infusion broth and inoculated into brain heart infusion agar. After incubation in 5% $CO_2$ in an anaerobic atmosphere at 37° C. for 48 hours, *S. mutans* was cultured in brain heart infusion broth overnight under the same anaerobic condition. The concentration of the bacterial culture was adjusted to 0.30 at $OD_{600}$ using Synergy™ Multi-Detection Microplate Reader (BioTek Instruments Inc., USA).

Assessment of Bacterial Adhesion and Colonization

Each of the dentin sections (six per group) were placed in 24-well plates (Corning). Two milliliter aliquots of the 0.30 at $OD_{600}$ bacterial suspension were added to each well. The specimens were then incubated for 4 h at 37° C. in an anaerobic atmosphere. This incubation time was chosen for the determination of bacterial adherence because complete biofilm formation in oral cavity normally occurs in 2 to 4 hours (Li, et al., *J Appl Microbiol* (2004) 97(6):1311-8; Palmer, et al., *J Bacteriol* (2006) 188(11):4117-24). To determine growth and colonization of *S. mutans* ATCC 25175, dentin specimens treated with the different sCaP solutions were cultured for 8, or 24 hours.

After incubation, each section was washed three times with 5 ml of PBS to remove non-adhering bacterial cells. The samples were fixed for 1 hour using Trumps fixative (glutaraldehyde in a mixture of sodium cacodylate buffer), rinsed in PBS, and washed twice in PBS. The samples were dehydrated through a series of washes using increasing concentrations of ethanol (50-100%), and dried using DCP-1 critical point drying apparatus (Enton Scuum INC., USA).

Ten-fold serial dilutions were prepared. The treated (with solution B, C or D) and control sections (6 per group per time point, 8, 16 and 24 hours), were placed in 24-well plates. Two milliliter aliquots of the 10-fold serial diluted bacterial culture were added to each plate. The initial concentration observed after 16 hours was 10 times less than that observed after 8 hours, and the concentration after 24 hours was 10 times less than after 16 hours. The specimens were then incubated at 37° C. in an anaerobic atmosphere. The samples were taken out from the plates after cultured for 8, 16, or 24 hours. The samples were fixed and dried as described above.

The specimens were sputter-coated with gold and viewed under a scanning electron microscope (JEOL JSM-5400; JEOL USA, Inc., Peabody, Mass.; and Hitachi S-3500N; Hitachi, Ltd., Tokyo, Japan). Ten images per sample were taken randomly with the same SEM working conditions (magnification and same working distance).

A Bioquant Nova Advanced Image Analysis apparatus (200 R&M Biometrics, Inc.) was used to count the number of bacteria on each dentin surface. The SEM images were loaded in Bioquant program to download sequential images. The manual measurement function was used to count the bacteria number on each image. Bacterial counting involved 10 random areas for each specimen.

One of the main problems in the study of bacterial attachment is the accurate quantification of the number of bacteria on a surface. The measurement of the accumulation of bacteria on the surfaces were generally performed by counting the bacterial colonies or by turbidity measurement after sonicating bacteria from the samples and culturing for a period of time (Chou, et al., *Implant Dent* (2007) 16(1):89-100; Li, et al., *J Dent Res* (1994) 73(10):1615-26; Montanaro, et al., *Biomaterials* (2004) 25(18):4457-63). This method has the advantage of being able to measure the total bacteria on each sample. However, this method involves removal of cells from the surface by physical forces (e.g. ultrasound, vortexing or grinding) which may result in loss of cell viability or incomplete detachment. Scherba, et al., *Appl Environ Microbiol* (1991) 57(7):2079-84 reported that ultrasound, even in the low frequency range of 26 kHz, could kill bacteria (*E. coli, S. aureus, Bacillus subtilis* and *Pseudomonas aeruginosa*). Therefore, this method could cause loss of some of the original data, leading to an underestimation of the bacteria population. The direct counting method used may minimize the under estimation of bacteria population.

Statistical Analysis

XRD, SEM, FT-IR and bacteria population were assessed by SPSS15.0 using one-way ANOVA followed by Student-Newman-Keuls or Dunnett's T3 post hoc. Dissolution experiment statistical analysis was conducted using MANOVA test within SAS 9.2 software. $\alpha=0.05$.

Results

Morphology of Treated and Control Dentin Surfaces.

Figure 9A:
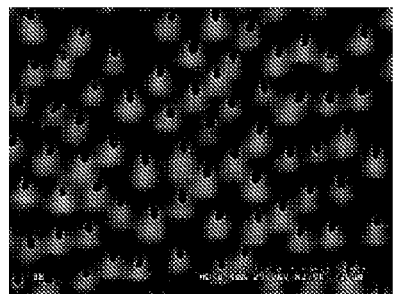
FIG. 9 depicts SEM images of dentin surfaces after immersion in distilled water (control) (1A, 1B), in solution A (1C, 1D), in solution B (1E, 1F) and in solution C (1G and 1H). After immersion, deposited crystals were seen on the dentin surfaces and inside dentin tubules. The diameters of the dentin tubules decreased. (1A, 1C, 1E and 1G magnification ×2K; 1B, 1D, 1F and 1H magnification×20K).
Figure 9B:
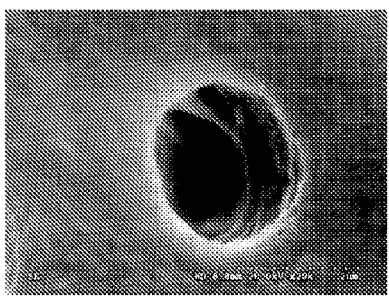
Figure 9C:
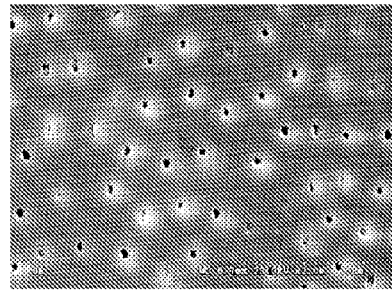
Figure 9D:
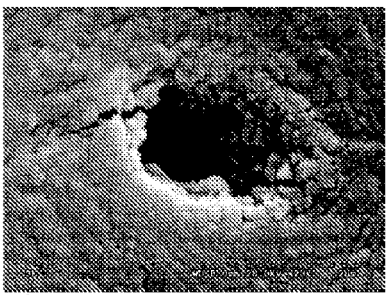
Figure 9E:
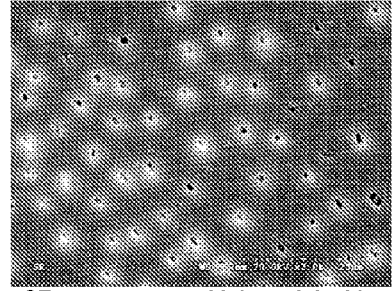
Figure 9F:
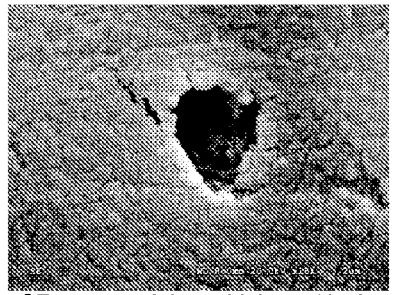
Figure 9G:
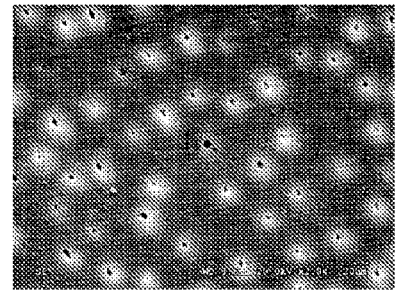
Figure 9H:
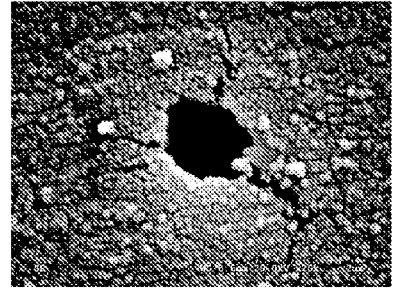

SEM image showed differences in surface morphology between the control and surfaces treated with sCaP solutions, indicating deposition of a coating on the surfaces treated with sCaP solutions (FIG. 9B compared with FIGS. 9D, 9F and 9H). The amount of the crystals deposited on the surfaces depends on the composition, pH and concentration of the solution. Surfaces treated with solutions B and C with lower pH (5.5), compared to surfaces treated with solution (A) with higher pH (7) had higher amounts of deposits (FIG. 9D compared to FIGS. 9F and 9H), and the surfaces treated with solutions containing higher concentrations of $F^-$ and $Zn^{2+}$ ions (solution C) had higher amount of deposits (FIG. 9H vs FIG. 9F).

Apatite on Dentin Surfaces

Figure 10:
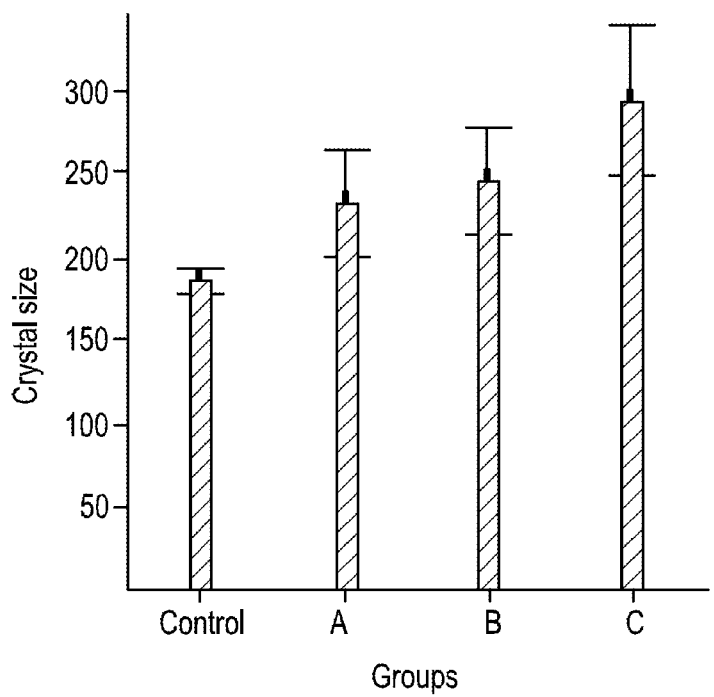
FIG. 10 provides graphs showing the crystallite size of apatite scraped from control and treated dentin surfaces The symbols and bars represent the means and standard deviations (n=6). The crystallite size between control and B treated and between control and C treated were significantly different (ANOVA and pariwise t-test).

No significant difference in the apatite crystallite size was observed in the XRD profiles among the three treated dentin surfaces and between control and solution A treated surfaces. However, there was a significant difference ($P<0.05$) between control and surfaces treated with solution B, and between control and surfaces treated with solution C ($p<0.01$). The mean ($\pm SD$) crystallite size (in Angstrom) for apatite crystals were $187\pm7$ for control surfaces; $232\pm31$, $246\pm31$, and $295\pm43$ for apatite crystals from surfaces treated with solutions A, B and C, respectively (FIG. 10).

FT-IR Spectra of Control and Treated Dentin Surfaces.

Figure 11A:
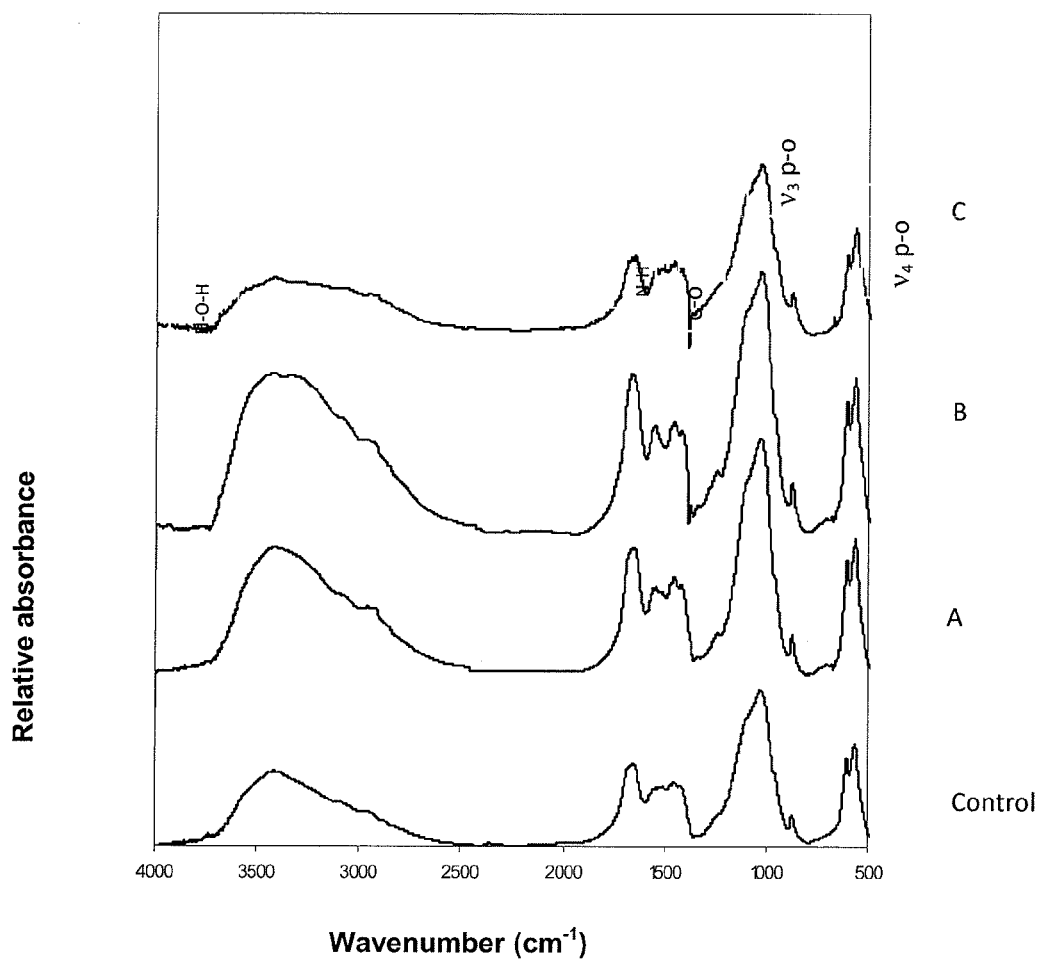
FIG. 11 provides FT-IR spectra of the materials scraped from the treated and control dentin surfaces: (A) A treated, (B) B treated and (C) C treated.
FIG. 11B. FT-IR spectra between 1300 $cm^{-1}$ and 500 $cm^{-1}$ showing greater resolution of v3P—O absorption bands (in 1102, 1065, 1027 $cm^{-1}$) in the spectra of materials scraped from dentin surface treated with solution C.
Figure 11B:
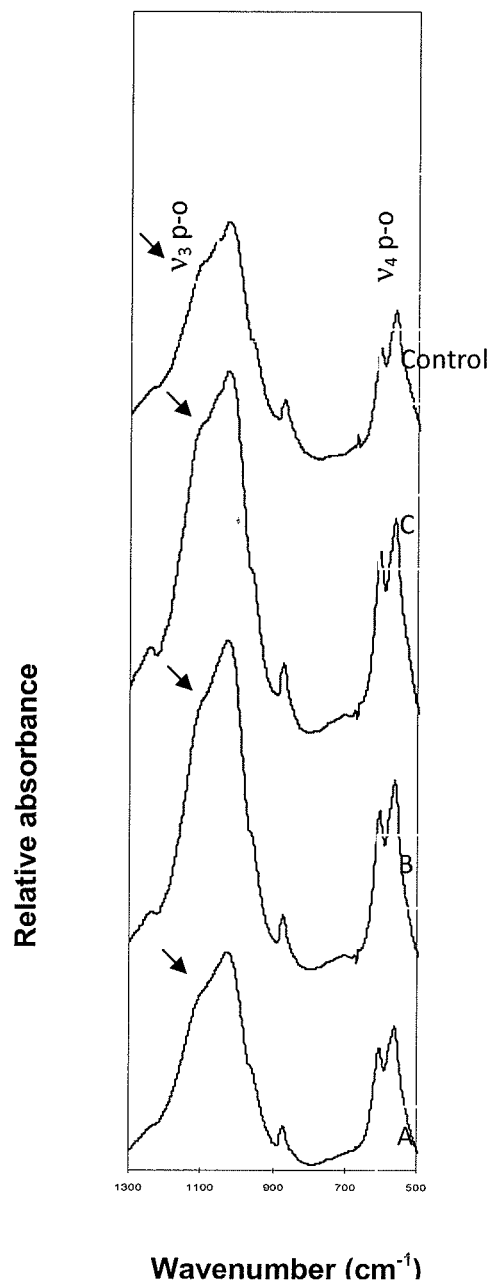
Figure 12:
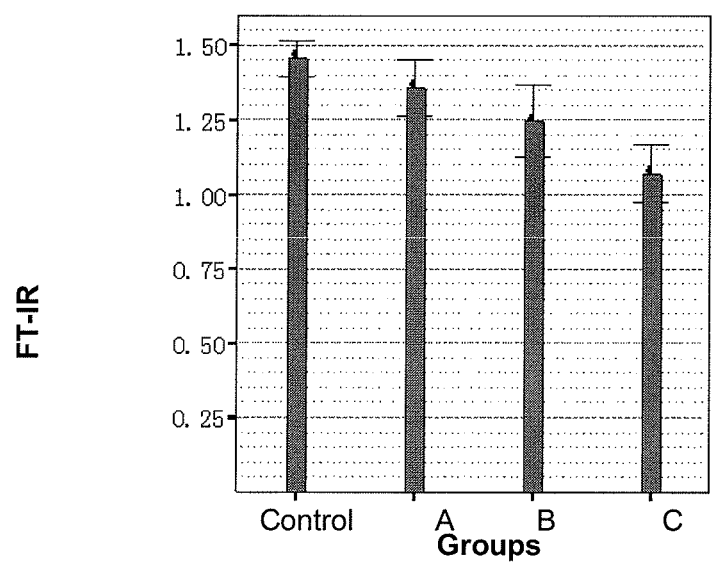
FIG. 12 demonstrates that the ratio of the organic phase (represented by the N—H absorption band from amide groups of collagen) to the inorganic or apatite phase (represented by the C—O absorption bands from the carbonate groups in carbonate apatite) in the spectra (FIG. 3) of materials scraped from the control and treated dentin surfaces. The symbols and bars represent the means and standard deviations (n=6). The organic/inorganic ratio between that of the control and B treated, between that of the control and the C treated and between that of A and C treated surfaces were significantly different.

FT-IR spectra of the materials scraped from the treated and control dentin surfaces showed typical spectra of carbonate apatite (LeGeros, et al., *Dev Appl Spectrosc* (1970) 7B:3-12; LeGeros Z R (1981). Biological apatites, Crystal Growth 1:45-55) showing absorption bands attributed to C—O (for the $CO_3$ group) at about $1510\ cm^{-1}$, $1450\ cm^{-1}$ and $873\ cm^{-1}$ and P—O (for the $PO_4$ group) at about $1100\ cm^{-1}$ to $1027\ cm^{-1}$, $603\ cm^{-1}$ and $562\ cm^{-1}$. In addition, an absorption band at $1653\ cm^{-1}$ attributed to the N—H, for the amide group in the organic phase (collagen) was also present (FIG. 11A). However, apatite from a surface treated with solution B or C showed a higher resolution of the absorption band of P—O stretching mode (1102, 1065, 1027 $cm^{-1}$) compared to those from control surface or surfaces treated with solution A (FIG. 11B). The resolution was higher for surfaces treated with C than with B. The organic/inorganic ratio represented by the N—H/C—O absorption band intensity ratios were $1.5\pm0.06$ for the control surface; $1.4\pm0.09$, $1.2\pm0.11$, and $1.1\pm0.09$ for surfaces treated with solutions A, B and C, respectively. No significant difference in the intensity ratios of N—H and C—O absorption bands between that of control and that of A treated surfaces and between A treated and B treated surfaces. However, there was a significant difference between the N—H/C—O intensity ratios of the control and the B surfaces, between the control and the C treated surfaces, and between A and the C treated surfaces (FIG. 12).

Dissolution Properties of Control and Dentin Surfaces

Figure 13:
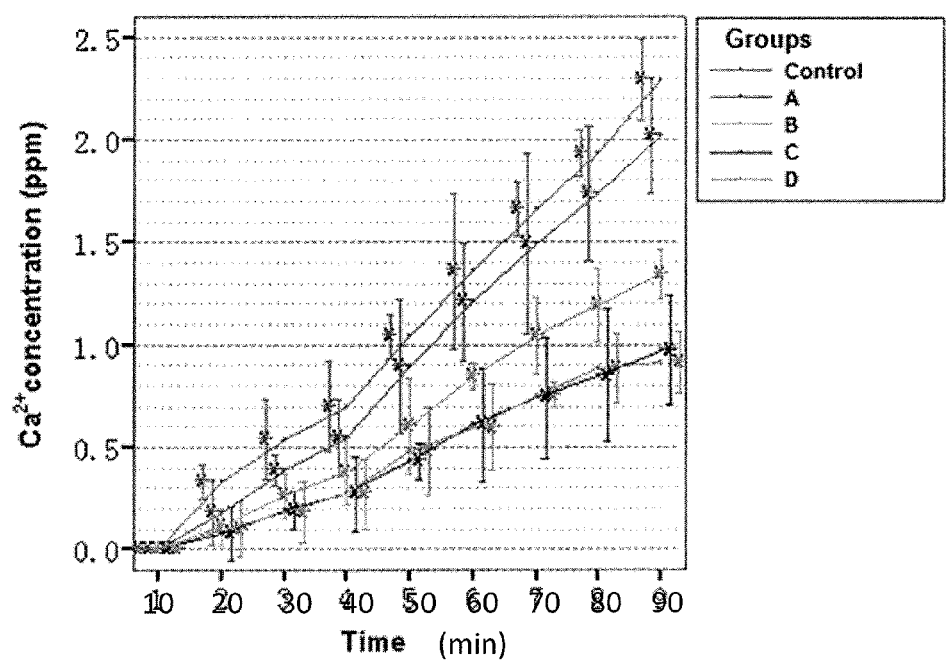
FIG. 13 provides dissolution curves showing comparative $Ca^{2+}$ ion concentration released in the acidic buffer from the control and treated dentin surfaces. The amount of $Ca^{2+}$ ions released in 60 min in acidic buffer was higher for the dentin surfaces treated with DDW (control) or that treated with solution A compared with surfaces treated with solution B or solution C. The surfaces treated with solution C exhibited the lowest value. *p<0.01, n=3 for each group.

The dissolution curves (amount of $Ca^{2+}$ ions released with time) showed that the amount of Ca ions released in 60 min in acidic buffer was higher for the control dentin surfaces and the surfaces treated with solution A compared with surfaces treated with solution B or solution C. The surfaces treated with solution C exhibited the lowest value. *$p<0.01$, n=3 for each group (MANOVA test) (FIG. 13).

Inhibition of Bacterial Attachment

Figure 14A:
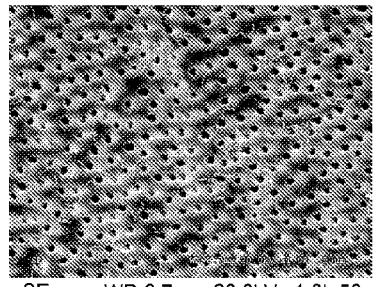
FIG. 14 provides SEM images showing greater population of *S. mutans* on control dentin (6A, 6C and 6E) compared to those treated with solution B (6B, 6D and 6F). A greater number of bacteria attached and grew into the open dentin tubules on the control dentin surfaces (6C and 6E) compared with those observed on the occluded dentin tubules of dentin treated with solution B (6D and 6F). Dentin surfaces treated with solution D (6H) compared to control (6G) showed higher number of occluded dentin tubules but the bacterial population was not significantly less. (6A and 6B magnification×1K; 6C and 6D magnification×6K; 6E and 6F magnification× 10K; 6G and 6H magnification×2K).
Figure 14B:
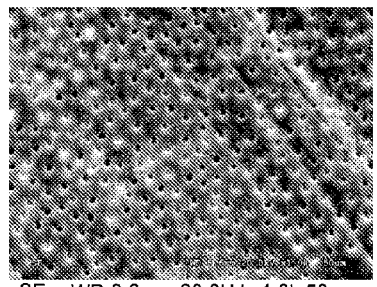
Figure 14C:
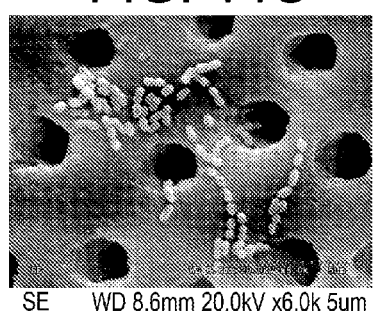
Figure 14D:
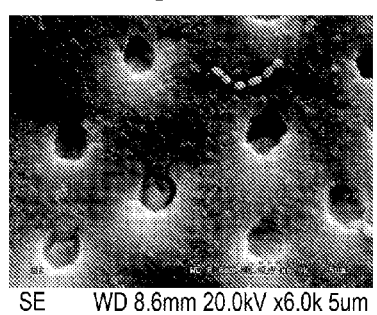
Figure 14E:
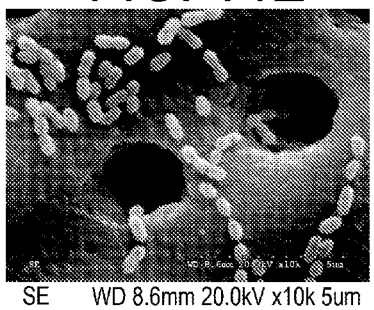
Figure 14F:
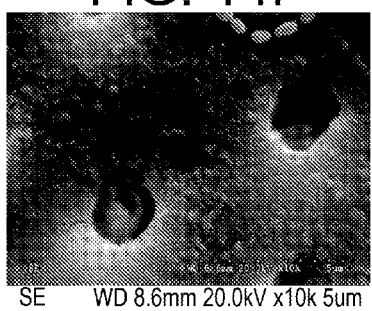
Figure 14G:
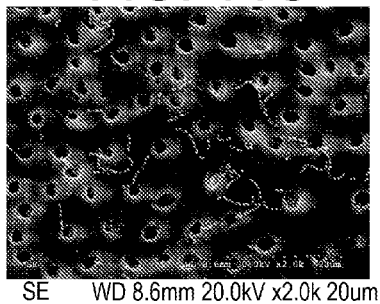
Figure 14H:
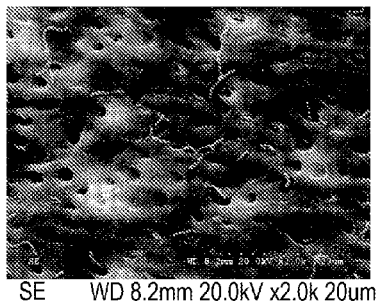

The population of S. mutans ATCC 25175 on control dentin surfaces (FIGS. 14A, 14C and 14E) was greater than that on the dentin surfaces treated with solutions B (FIGS. 14B, 14D and 14F) and C. Dentin sections treated with solution B or C showed inhibition of S. mutans ATCC 25175 attachments. A greater number of bacteria attached and grew into the open dentin tubules on the control dentin surfaces (FIGS. 14C and 14E) compared with that observed on dentin treated with solution B (FIGS. 14D and 14F) or C (data not shown). Occluded dentin tubules were observed on dentin treated with solutions B (FIG. 14D, 14F) or C. However, there was no visual difference between the population of adhering S. mutans ATCC 25175 on control (dentin surfaces treated with double distilled water) shown in FIG. 14G and dentin surfaces treated with solution D (without $Zn^{2+}$ ions) (FIG. 14H).

Figure 15:
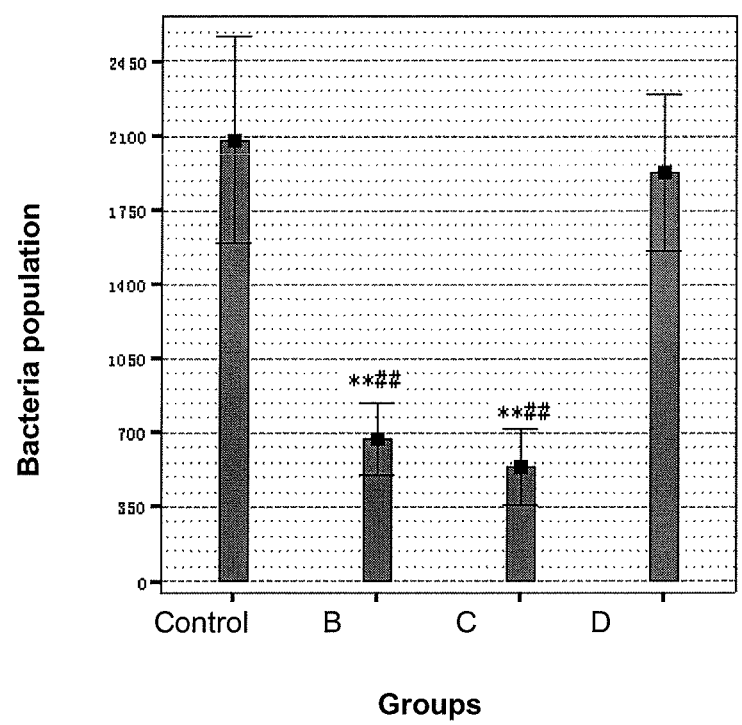
FIG. 15 provides graphs showing that the mean number for the bacteria attached on control dentin surfaces was significantly greater than on surfaces treated with solutions B or C after 4 hours in culture. The symbols and bars represent the means and standard deviations (n=6). The comparisons between D and B and between D and C also showed significant difference. There was no significant difference between control and D; nor between surfaces treated with solution B and those treated with solution C (p>0.05). **p<0.01, ##p<0.01.
Figure 16A:
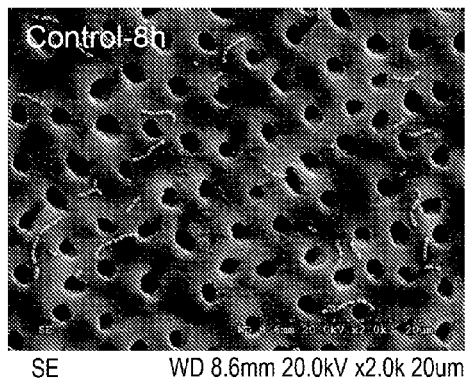
FIG. 16 provides SEM images showing considerably less population of *S. mutans* ATCC 25175 on dentin surfaces treated with solution B (B-8 h, B-16 h and B-24 h) compared to that on the control dentin surfaces after 8, 16 and 24 hours in culture (control-8 h, control-16 h and control-24 h). The dentin tubule diameters were also less on the surface treated with solution B compared to control (magnification×2K)
Figure 16B:
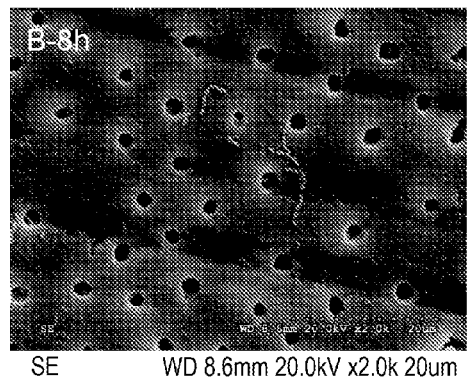
Figure 16C:
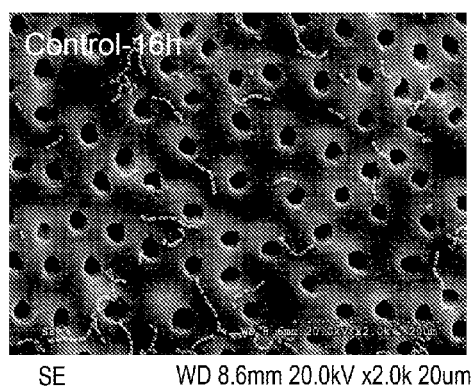
Figure 16D:
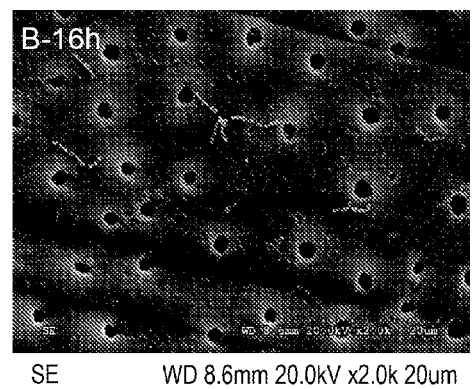
Figure 16E:
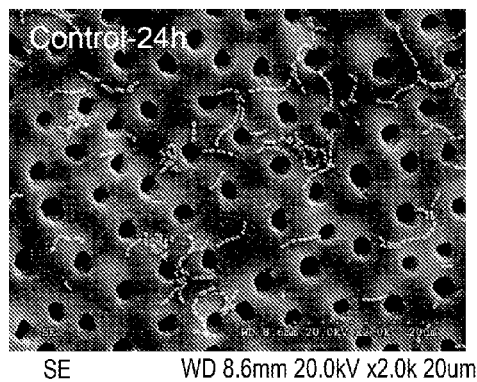
Figure 16F:
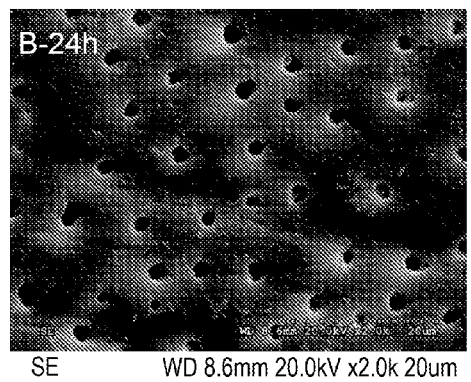

Statistical analysis also showed that the mean number for the bacteria attached on each of the dentin surfaces treated with solutions B or C was significantly less than that on the control dentin surfaces or those treated with solution A. There was no significant difference in the mean number for bacteria attachment between B and C and between A4 and A1 (FIG. 15).

Inhibition of Bacterial Growth and Colonization

SEM images showed that the population of S. mutans ATCC 25175 on dentin surfaces treated with solutions B (FIGS. 8B-8 h, B-16 h and B-24 h) or C (data not shown) was much less compared to that on the control dentin surfaces or those treated with solution D after 8, 16 and 24 hours in culture (FIG. 16 control-8 h, control-16 h and control-24 h).

Figure 17A:
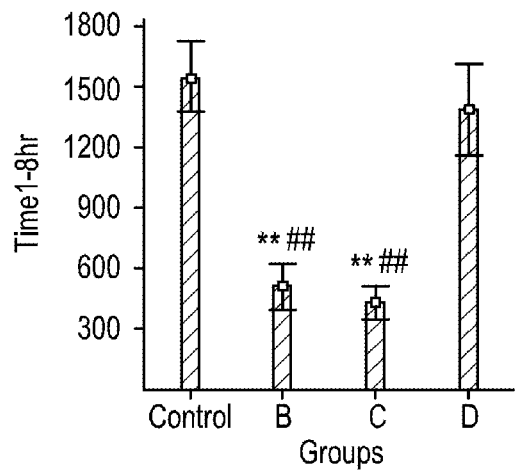
FIG. 17 provides graphs showing the mean number for *S. mutans* ATCC 25175 colonization on control dentin surfaces and surfaces treated with solutions B, C or D after 8 hours in cultured with the bacteria concentration of 0.3 at $OD_{600}$ diluted 10 times, after 16 hours with the bacteria concentration diluted 100 times, and after 24 hours with the bacteria concentration diluted 1000 times. The symbols and bars represent the means and standard deviations (n=6). After 8, 16 or 24 hours culture, the comparisons between control and treatments with solution B and between control and treatments with solution C showed significant difference. The comparisons between D and B and between D and C also showed significant difference. There was no significant difference between control and D; nor between surfaces treated with solution B and solution C. **p<0.01, #p<0.05.
Figure 17B:
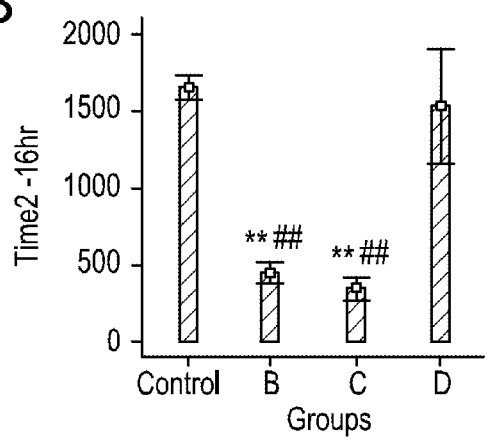
Figure 17C:
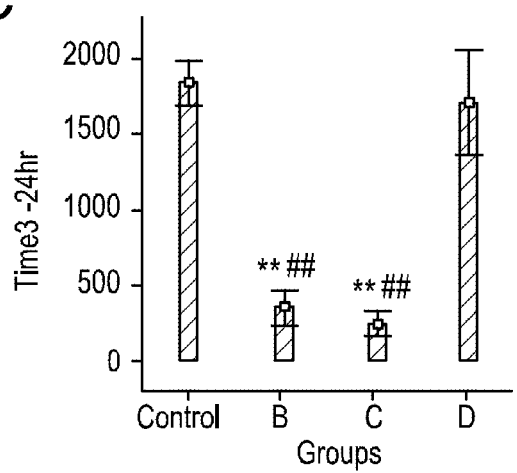
Figure 18A:
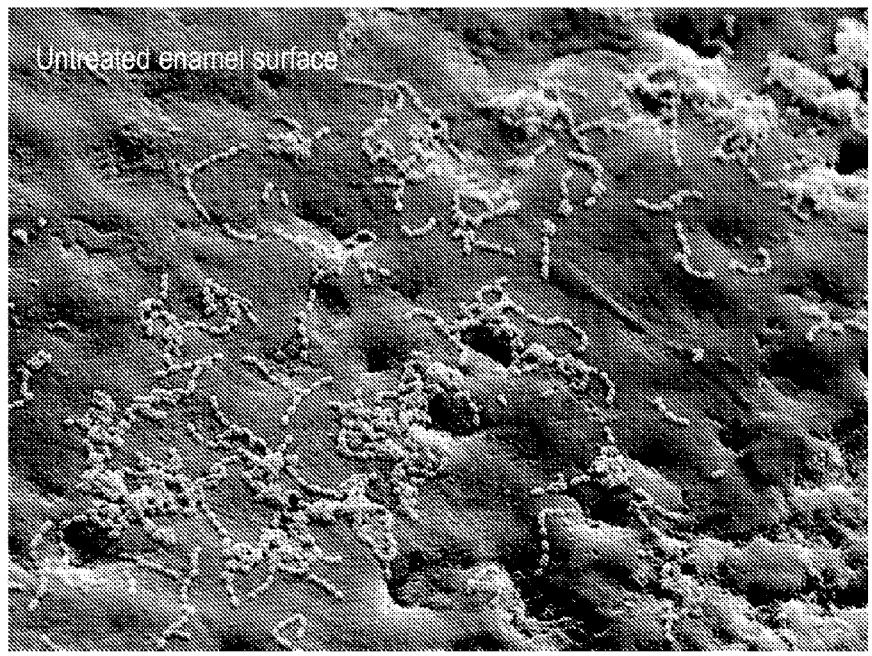
FIG. 18 provides SEM images of enamel surfaces that are untreated and that have been treated with a sCaP solution as described herein.
Figure 18B:
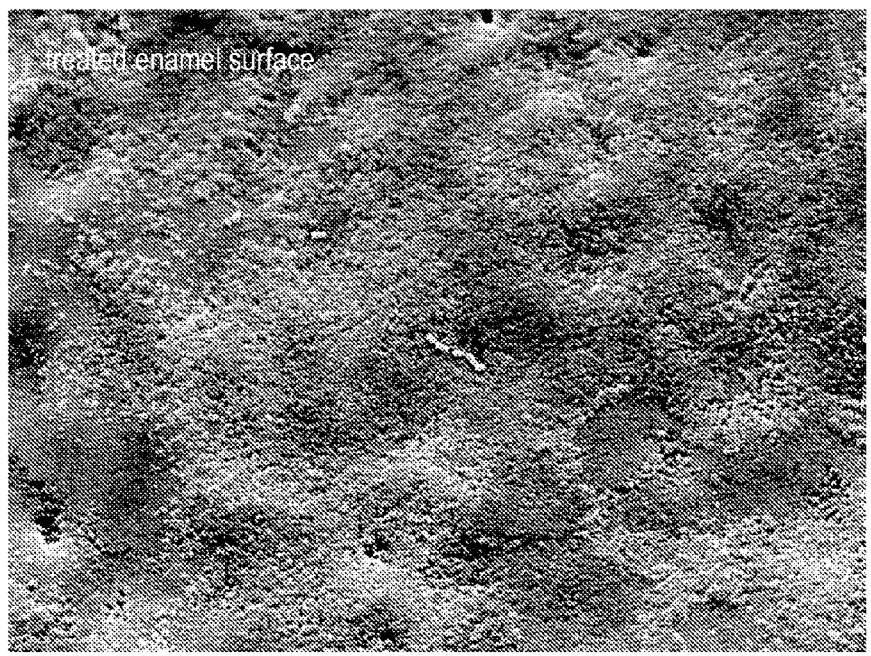
Figures 1, 19A:
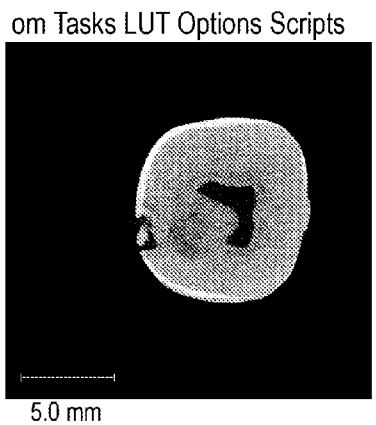
FIG. 19A provides microCT images of (A, C) untreated and (B, D) treated proximal caries. 100 slices (A, B) and 200 slices (C, D) above baseline.
Figures 2, 19A:
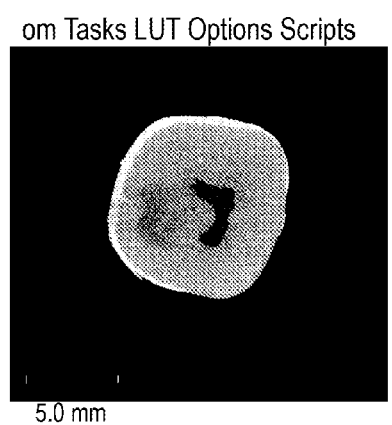
Figures 3, 19A:
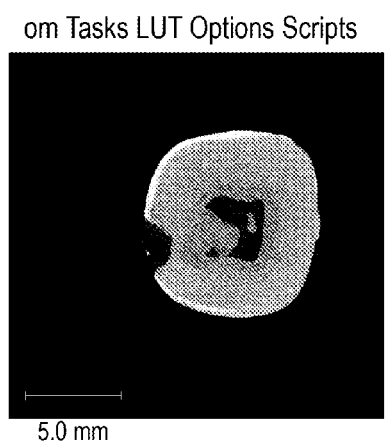
Figures 4, 19A:
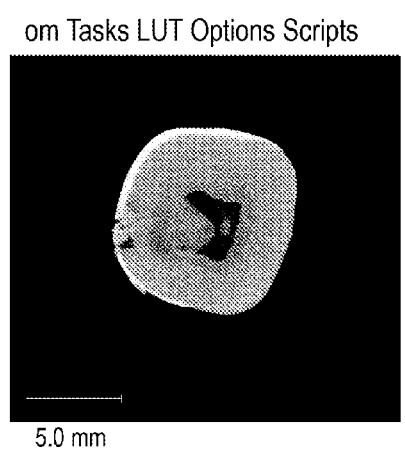
Figures 1, 19B:
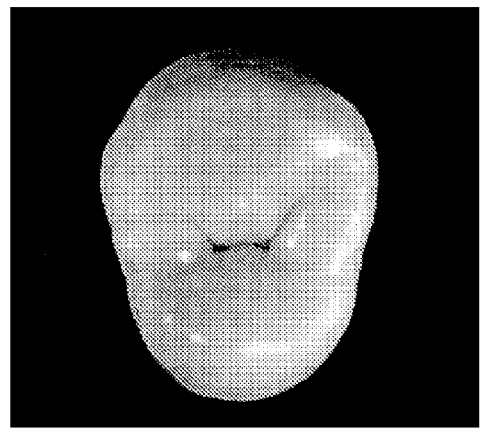
FIG. 19B provides SEM images of (a) untreated and (b) treated natural fissures.
Figures 2, 19B:
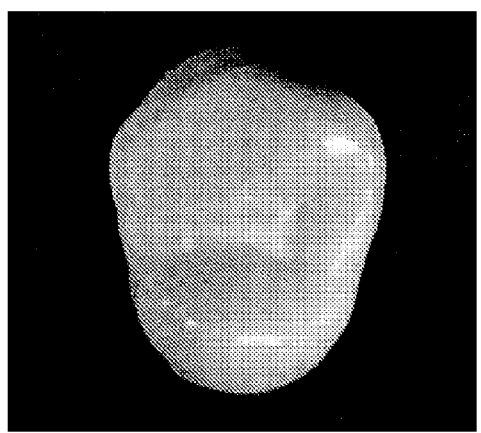

Using Bioquant, the mean number for the bacteria colonized on each of the dentin surfaces treated with solutions B or C showed significant difference compared to those treated with solution D or the control dentin surfaces at the 3 time points (FIGS. 17A, 17B and 17C). Solution C compared to solution B showed the greater inhibiting effect on S. mutans ATCC 25175 colonization. Although no significant difference was observed between surfaces treated with solutions B or C after 8 hours and 24 hours culture, the dentin surfaces treated with solution C appeared to have less bacterial colonization (FIGS. 17A and 17C).

EXAMPLE 3

The efficacy of calcium phosphate (CaP) solutions containing either Zn, F or both ions was determined in both minimizing dissolution of enamel surfaces and providing an antibacterial surface.

Materials and Methods

Saturated calcium phosphate solutions (sCaP) were prepared using calcium deficient apatite (CDA) ($Ca(OH)_2$+$Na_2HPO_4 \rightarrow (Ca,Na)_{10}(PO_4,HPO_4)_6(OH)_2$) at a temperature of 90° C. for a reaction time of 2 hours. Acidic saturated calcium phosphate solutions (sCaP) were prepared as follows:

Solution A: CDA+NaF+$ZnCl_2$ dissolved in HCl.
Solution B: CDA+NaF dissolved in HCl.
Solution C: CDA+$ZnCl_2$ dissolved in HCl.
Solution D: CDA dissolved in HCl All the solutions were adjusted to pH 5.5 using sodium hydroxide (1M).

Analysis of CaP Solutions

ICP was used for $Ca^{2+}$, P (for $PO_4^{3-}$), $Zn^{2+}$ ion concentrations and a fluoride electroder was used for the $F^-$ ion concentration.

Treatment and Characterizaion of the Enamel Sections

The enamel sections were distributed randomly into 4 groups (n=19) and treated as follows: Groups A, B, C and D were treated with solutions A, B, C and D respectively, for 4 minutes and rinsed with DDW. They were tested for the effect of adsorbed albumin, a separate group of 7 enamel sections were immersed in bovine serum albumin for one minute and then treated with solution A for 4 minutes. Surface morphology was determined by SEM.

Determination of Anti-Bacterial Property

Bacteria of the strain S. mutans UA 159 were prepared. Bacterial adhesion and bacterial colonization were determined.

Statistical Analysis

Statistical analysis was performed using a one-way ANOVA. Post hoc multiple comparison was performed used Tukey's Studentized methods. Range (HSD) was tested within the SAS system. α=0.05

Dissolution Experiments

Comparative release of $Ca^{2+}$ ions after immersion into the buffer of treated and untreated groups was determined. The results demonstrated release of $Ca^{2+}$ at the following relative amounts:

CaP+F+Zn<CaP+F or CaP+Zn<CaP<Untreated

No significant difference was observed in the dissolution rate of enamel surfaces pre-treated with albumin or not pretreated.

Results

Figure 20A:
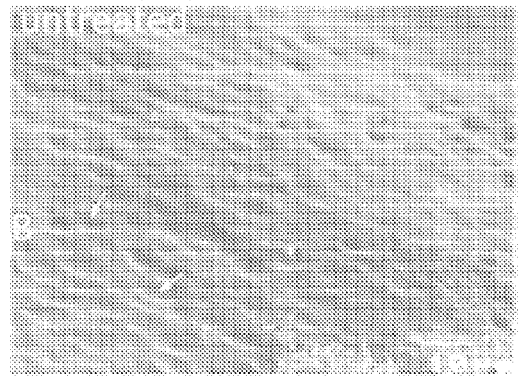
FIG. 20 demonstrates the concentration of $Ca^{2+}$ ions (expressed in ppm) released in the acidic buffer from untreated and groups treated with Alb+A, A, B, C, D solutions described in Example 3.
Figure 20B:
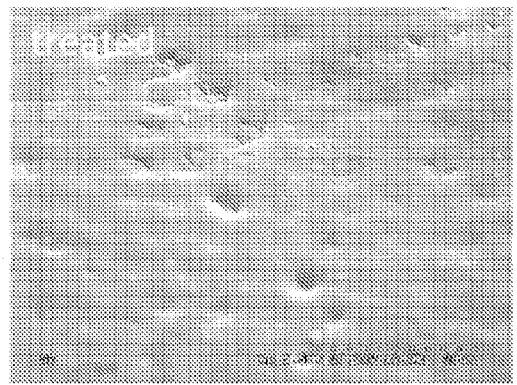
Figure 21:
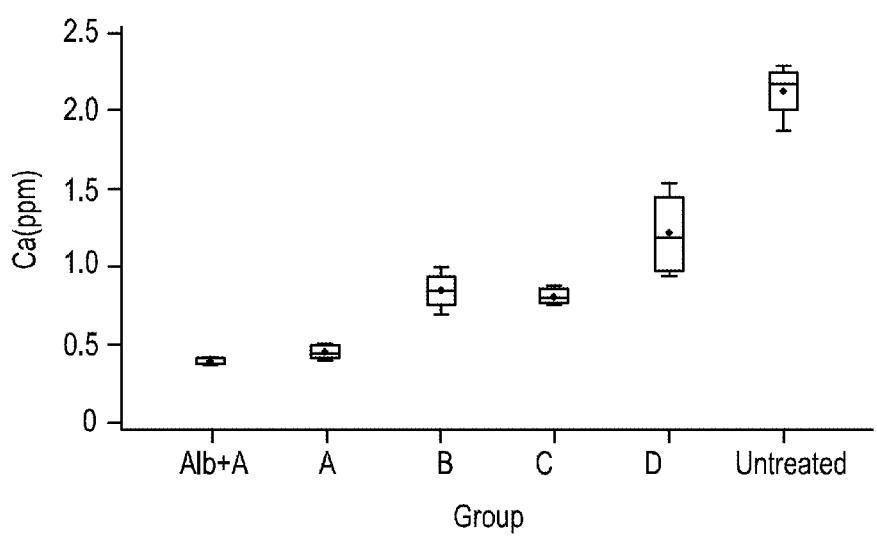
FIG. 21 demonstrates the concentration of $Ca^{2+}$ ions (expressed in ppm) released in the acidic buffer from untreated and groups treated with Alb+A, A, B, C, D solutions described in Example 3.
Figure 22:
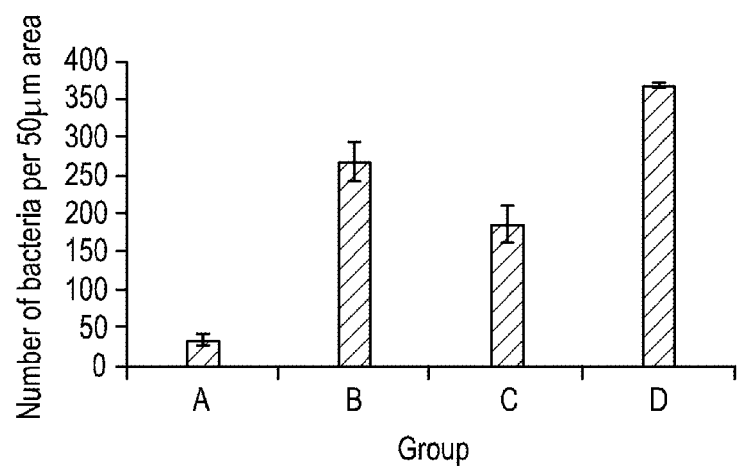
FIG. 22 provides the bacterial counts after 4 hour adhesion in groups treated with solutions A (CaP+F+Zn), B (CaP+F), C (CaP+Zn) and D (CaP).
Figure 23A:
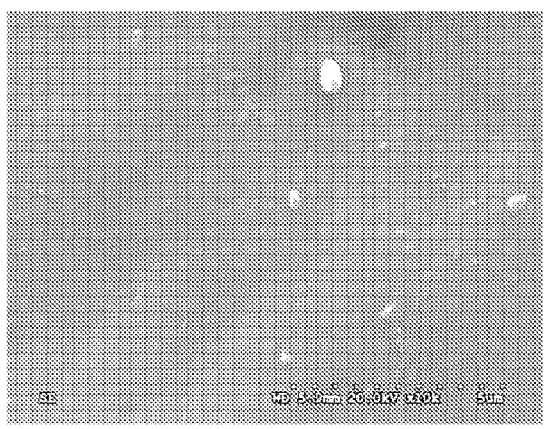
FIG. 23 provides SEM images showing bacterial adhesion after 4 hours in groups treated with solutions A, B, C and D at ×10 k.
Figure 23B:
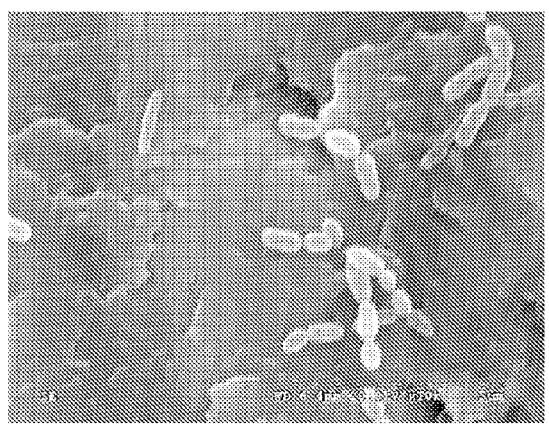
Figure 23C:
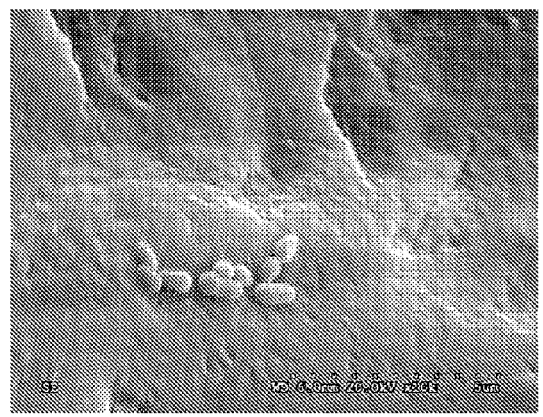
Figure 23D:
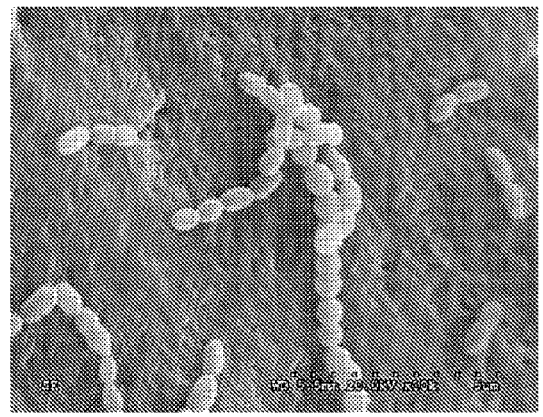
Figure 24:
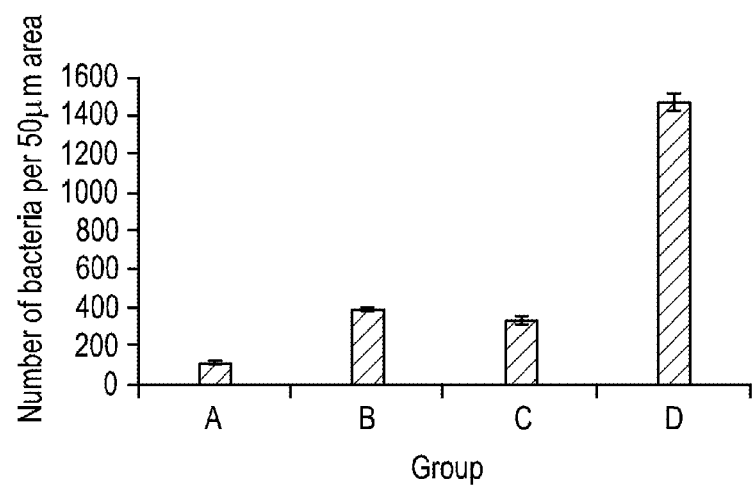
FIG. 24 provides the bacterial counts after 8 hour colonization in groups treated with solutions A (CaP+F+Zn), B (CaP+F), C (CaP+Zn) and D (CaP).
Figure 25A:
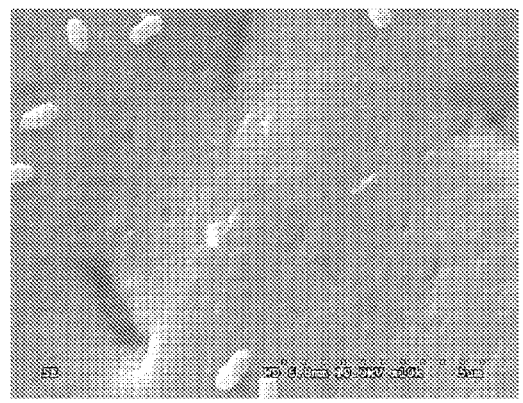
FIG. 25 provides SEM images showing bacterial colonization after 8 hours in groups treated with solutions A, B, C and D at ×10 k.
Figure 25B:
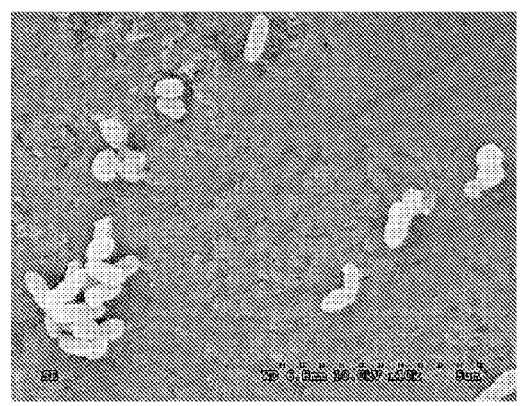
Figure 25C:
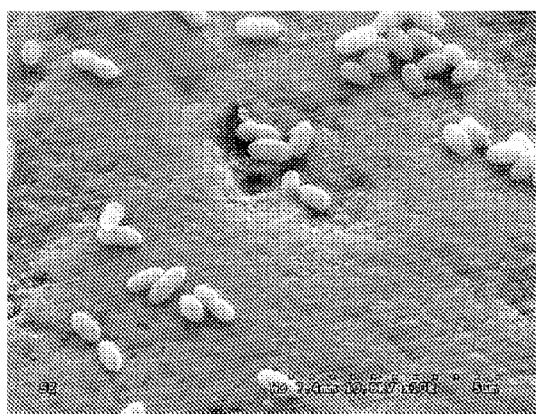
Figure 25D:
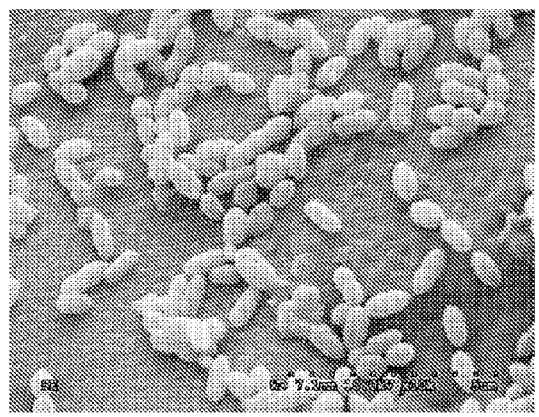
Figure 26A:
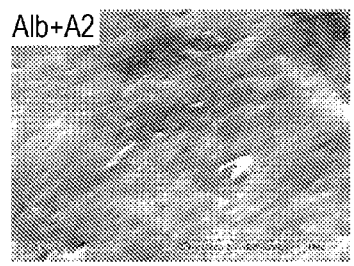
FIG. 26 provides SEM images showing bacterial colonization after 24 hours in groups treated with solutions Alb+A, A, B, C, D and group Untreated at ×10 k.
Figure 26B:
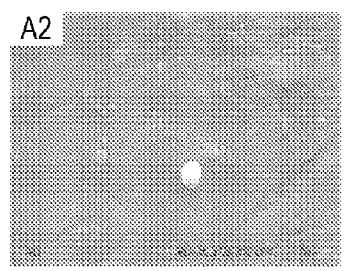
Figure 26C:
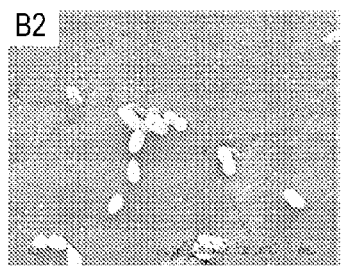
Figure 26D:
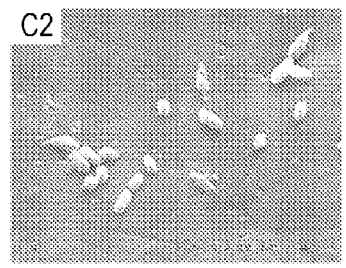
Figure 26E:
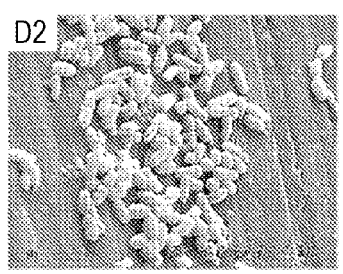
Figure 26F:
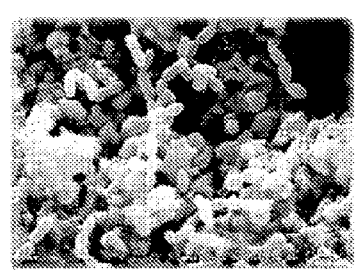
Figure 27:
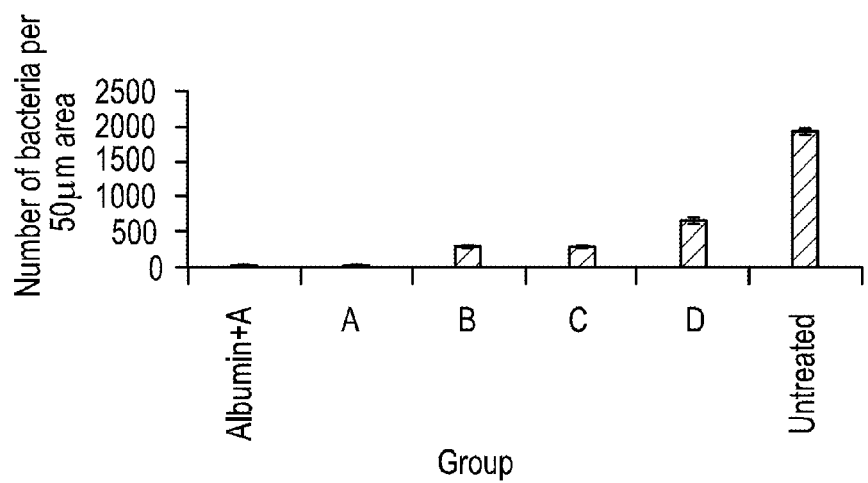
FIG. 27 provides the bacterial counts after 24 hours colonization in groups treated with solutions Albumin+a (Albumin+CaP+F+Zn), A (CaP+F+Zn), B (CaP+F), C (CaP+Zn), D (CaP) and group Untreated.
Figure 28:
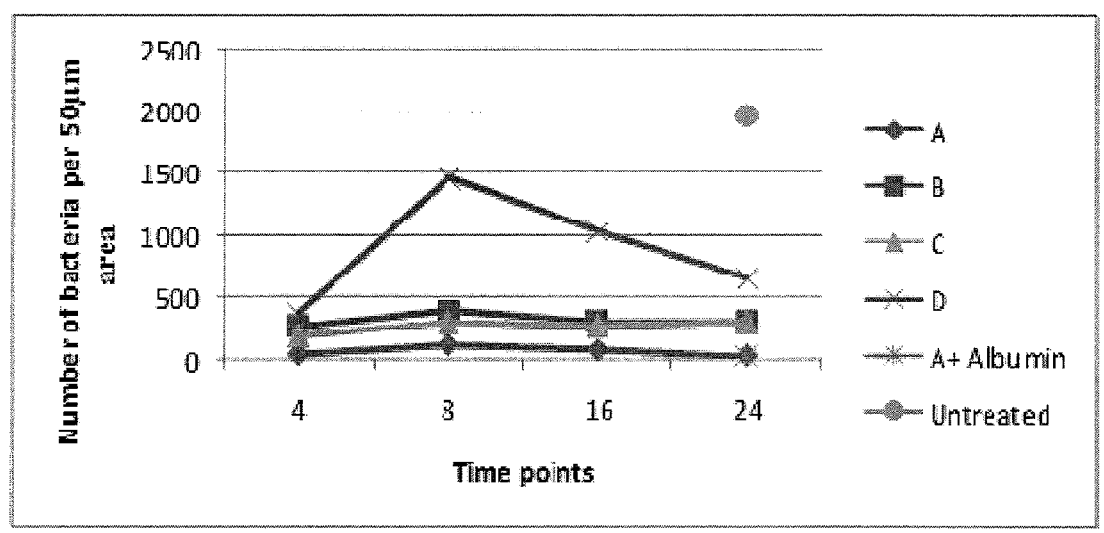
FIG. 28 is a combined graph showing bacterial count in different groups treated with solutions Albumin+A, A, B, C, D and group Untreated at different time points.

FIG. 20 demonstrates the concentration of $Ca^{2+}$ ions (expressed in ppm) released in the acidic buffer from untreated and groups treated with Alb+A, A, B, C, D solutions. FIG. 21 demonstrates the concentration of $Ca^{2+}$ ions (expressed in ppm) released in the acidic buffer from untreated and groups treated with Alb+A, A, B, C, D solutions. FIG. 22 provides the bacterial counts after 4 hr adhesion in groups treated with solutions A (CaP+F+Zn), B (CaP+F), C (CaP+Zn) and D (CaP). FIG. 23 provides SEM images showing bacterial adhesion after 4 hrs in groups treated with solutions A, B, C and D at ×10 k. FIG. 24 provides the bacterial counts after 8 hr colonization in groups treated with solutions A (CaP+F+Zn), B (CaP+F), C (CaP+Zn) and D (CaP). FIG. 25 provides SEM images showing bacterial colonization after 8 hrs in groups treated with solutions A, B, C and D at ×10 k. FIG. 26 provides SEM images showing bacterial colonization after 24 hrs in groups treated with solutions Alb+A, A, B, C, D and group Untreated at ×10 k. FIG. 27 provides the bacterial counts after 24 hrs colonization in groups treated with solutions Albumin+a (Albumin+CaP+F+Zn), A (CaP+F+Zn), B (CaP+F), C (CaP+Zn), D (CaP) and group Untreated. FIG. 28 is a combined graph showing bacterial count in different groups treated with solutions Albumin+A, A, B, C, D and group Untreated at different time points.

CaP solutions containing both $F^-$ and $Zn^{2+}$ ions are more effective in reducing solubility of enamel surfaces and in minimizing bacterial growth and colonization compared to CaP solutions containing either $F^-$ or $Zn^{2+}$ ions or CaP solutions not containing these ions. CaP solutions containing both $F^-$ and $Zn^{2+}$ ions may be more effective than CaP solutions containing either $F^-$ or $Zn^{2+}$ ions in the prevention and treatment of enamel caries compared to CaP solutions containing only $Zn^{2+}$ or $F^-$ or none.

We claim:

1. A method for increasing or promoting occlusion of dentin tubules on the surface of a tooth comprising providing a composition including a saturated calcium phosphate (sCaP) solution supersaturated with both F- and Zn-substituted calcium phosphates and having a pH of about 5.0 to 7.5.

2. A method according to claim 1 resulting in substantial occlusion of at least about 50% of dentin tubules present on the tooth surface.

3. A method according to claim 1 resulting in a mean occlusion of 50% or more of substantially all the dentin tubules present on the tooth surface.

4. A method for decreasing bacterial attachment to dentin tubules or decreasing bacterial attachment to the surface of a tooth comprising providing a composition including a saturated calcium phosphate (sCaP) solution supersaturated with both F- and Zn-substituted calcium phosphates and having a pH of about 5.0 to 7.5.

5. A method according to claim 4 resulting in reduction of at least about 50% of the number of bacteria attached to the dentin or to the surface the tooth as compared to a control.

6. A method for decreasing bacterial growth or colonization on the surface of a tooth comprising providing a composition including a saturated calcium phosphate (sCaP) solution supersaturated with both F- and Zn-substituted calcium phosphates and having a pH of about 5.0 to 7.5.

7. A method according to claim 6 resulting in reduction of at least about 50% of the number of bacteria presence on the surface the teeth as compared to a control.

8. A method for inhibiting tooth decay or inhibiting development of tooth hypersensitivity comprising providing a composition including a saturated calcium phosphate (sCaP) solution supersaturated with both F- and Zn-substituted calcium phosphates and having a pH of about 5.0 to 7.5.

9. A method for inhibiting acid dissolution of a tooth surface comprising providing a composition including a saturated calcium phosphate (sCaP) solution supersaturated with both F- and Zn-substituted calcium phosphates and having a pH of about 5.0 to 7.5.

10. A method according to claim 9 resulting in a reduction in the rate of acid dissolution of the tooth surface of at least about 70% compared to a control.

11. A composition that may be useful for one or more of increasing occlusion of dentin tubules, decreasing bacterial attachment to dentin tubules, decreasing bacterial growth or colonization on tooth surfaces including on dentin tubules, inhibiting tooth decay or inhibiting development of tooth hypersensitivity comprising a saturated calcium phosphate (sCaP) solution supersaturated with both F- and Zn-substituted calcium phosphates and having a pH of about 5.0 to 7.5.

* * * * *